(12) United States Patent
Vlegele et al.

(10) Patent No.: US 7,452,357 B2
(45) Date of Patent: Nov. 18, 2008

(54) SYSTEM AND METHOD FOR PLANNING TREATMENT OF TISSUE

(75) Inventors: James W. Vlegele, Cincinnati, OH (US); Robert P. Gill, Mason, OH (US); Joyce A. Duell, Loveland, OH (US); Mary E. Schramm, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 749 days.

(21) Appl. No.: 10/971,419

(22) Filed: Oct. 22, 2004

(65) Prior Publication Data

US 2006/0089624 A1 Apr. 27, 2006

(51) Int. Cl.
*A61B 18/18* (2006.01)
(52) U.S. Cl. .............................. 606/32; 606/41; 600/439
(58) Field of Classification Search ............. 606/32–34, 606/41, 48–50; 600/439, 459
See application file for complete search history.

(56) References Cited

U.S. PATENT DOCUMENTS

| | | | |
|---|---|---|---|
| 4,315,514 A | 2/1982 | Drewes et al. | |
| 4,323,077 A | 4/1982 | Smith | |
| 4,484,569 A | 11/1984 | Driller et al. | |
| 4,646,756 A | 3/1987 | Watnough et al. | |
| 4,757,820 A | 7/1988 | Itoh | |
| 4,787,394 A | 11/1988 | Ogura | |
| 4,818,954 A | 4/1989 | Flachenecker et al. | |
| 4,849,692 A | 7/1989 | Blood | |
| 4,858,613 A | 8/1989 | Fry et al. | |
| 4,932,414 A | 6/1990 | Coleman et al. | |
| 4,945,305 A | 7/1990 | Blood | |
| 4,951,653 A | 8/1990 | Fry et al. | |

(Continued)

FOREIGN PATENT DOCUMENTS

JP 10-14967 1/1998

(Continued)

OTHER PUBLICATIONS

Hill, C.R. et al., Lesion Development In Focused Ultrasound Surgery: A General Model, Ultrasound in Med. & Biol., 1994, pp. 259-269, vol. 20, No. 3, Elsevier Science Ltd, New York, USA.

(Continued)

*Primary Examiner*—Michael Peffley
(74) *Attorney, Agent, or Firm*—Thompson Hine LLP

(57) ABSTRACT

A method and system for treating tissue with a surgical device includes the steps of displaying an image created by collecting imaging data from an imaging device, selecting at least one tissue target from the image, determining the effective treatment volume of the surgical device and determining a treatment modality for treating the tissue target with the surgical device, where the treatment modality is made up of at least one target treatment volume. The method may also include the steps of determining the position and orientation of the imaging device, the image and the surgical device, indicating the trajectory of the surgical device with respect to the image on the display screen, inserting the surgical device in the patient based upon the trajectory and treating the tissue target. The method may further include indicating the target treatment volumes on the display screen.

32 Claims, 28 Drawing Sheets

U.S. PATENT DOCUMENTS

| | | |
|---|---|---|
| 4,955,365 A | 9/1990 | Fry et al. |
| 4,955,366 A | 9/1990 | Uchiyama et al. |
| 4,960,107 A | 10/1990 | Aida et al. |
| 4,984,575 A | 1/1991 | Uchiyama et al. |
| 4,986,275 A | 1/1991 | Ishida et al. |
| RE33,590 E | 5/1991 | Dory |
| 5,015,929 A | 5/1991 | Cathignol et al. |
| 5,036,855 A | 8/1991 | Fry et al. |
| 5,054,470 A | 10/1991 | Fry et al. |
| 5,056,523 A | 10/1991 | Hotchkiss, Jr. et al. |
| 5,065,740 A | 11/1991 | Itoh |
| 5,078,144 A | 1/1992 | Sekino et al. |
| 5,080,101 A | 1/1992 | Dory |
| 5,080,102 A | 1/1992 | Dory |
| 5,095,907 A | 3/1992 | Kudo et al. |
| 5,095,910 A | 3/1992 | Powers |
| 5,143,073 A | 9/1992 | Dory |
| 5,143,074 A | 9/1992 | Dory |
| 5,149,319 A | 9/1992 | Unger |
| 5,150,711 A | 9/1992 | Dory |
| 5,150,712 A | 9/1992 | Dory |
| 5,158,070 A | 10/1992 | Dory |
| 5,158,071 A | 10/1992 | Umemura et al. |
| 5,203,333 A | 4/1993 | Nomura |
| 5,209,221 A | 5/1993 | Riedlinger |
| 5,240,005 A | 8/1993 | Viebach |
| 5,295,484 A | 3/1994 | Marcus et al. |
| 5,304,115 A | 4/1994 | Pflueger et al. |
| 5,311,869 A | 5/1994 | Okazaki |
| 5,354,258 A | 10/1994 | Dory |
| 5,391,140 A | 2/1995 | Schaetzle et al. |
| 5,391,197 A | 2/1995 | Burdette et al. |
| 5,402,792 A | 4/1995 | Kimura |
| 5,409,002 A | 4/1995 | Pell |
| 5,431,663 A | 7/1995 | Carter |
| 5,435,304 A | 7/1995 | Oppelt et al. |
| 5,435,311 A | 7/1995 | Umemura et al. |
| 5,443,069 A | 8/1995 | Schaetzle |
| 5,448,994 A | 9/1995 | Iinuma |
| 5,471,988 A | 12/1995 | Fujio et al. |
| 5,474,071 A | 12/1995 | Chapelon et al. |
| 5,483,961 A | 1/1996 | Kelly et al. |
| 5,485,839 A | 1/1996 | Aida et al. |
| 5,492,126 A | 2/1996 | Hennige et al. |
| 5,514,130 A | 5/1996 | Baker |
| 5,520,188 A | 5/1996 | Hennige et al. |
| 5,522,869 A | 6/1996 | Burdette et al. |
| 5,524,620 A | 6/1996 | Rosenschein |
| 5,526,815 A | 6/1996 | Granz et al. |
| 5,526,822 A | 6/1996 | Burbank et al. |
| 5,540,648 A | 7/1996 | Yoon et al. |
| 5,540,656 A | 7/1996 | Pflueger et al. |
| 5,545,195 A | 8/1996 | Lennox et al. |
| 5,549,638 A | 8/1996 | Burdette |
| 5,569,241 A | 10/1996 | Edwards |
| 5,571,088 A | 11/1996 | Lennox et al. |
| 5,573,497 A | 11/1996 | Chapelon |
| 5,575,772 A | 11/1996 | Lennox |
| 5,575,789 A | 11/1996 | Bell et al. |
| 5,582,588 A | 12/1996 | Sakurai et al. |
| 5,588,432 A | 12/1996 | Crowley |
| 5,590,657 A | 1/1997 | Cain et al. |
| 5,601,526 A | 2/1997 | Chapelon et al. |
| 5,620,479 A | 4/1997 | Diederich |
| 5,624,382 A | 4/1997 | Oppelt et al. |
| 5,628,743 A | 5/1997 | Cimino |
| 5,643,179 A | 7/1997 | Fujimoto |
| 5,647,373 A | 7/1997 | Paltieli |
| 5,649,547 A | 7/1997 | Ritchart et al. |
| 5,658,272 A | 8/1997 | Hasson et al. |
| 5,665,054 A | 9/1997 | Dory |
| 5,666,954 A | 9/1997 | Chapelon et al. |
| 5,676,692 A | 10/1997 | Sanghvi et al. |
| 5,687,729 A | 11/1997 | Schaetzle |
| 5,694,936 A | 12/1997 | Fujimoto et al. |
| 5,697,897 A | 12/1997 | Buchholtz et al. |
| 5,699,804 A | 12/1997 | Rattner |
| 5,703,922 A | 12/1997 | Rattner |
| 5,720,287 A | 2/1998 | Chapelon et al. |
| 5,722,411 A | 3/1998 | Suzuki et al. |
| 5,728,062 A | 3/1998 | Brisken |
| 5,730,129 A | 3/1998 | Darrow et al. |
| 5,733,315 A | 3/1998 | Burdette et al. |
| 5,735,280 A | 4/1998 | Sherman et al. |
| 5,735,796 A | 4/1998 | Granz et al. |
| 5,738,635 A | 4/1998 | Chapelon et al. |
| 5,743,862 A | 4/1998 | Izumi |
| 5,743,863 A | 4/1998 | Chapelon |
| 5,746,224 A | 5/1998 | Edwards |
| 5,759,162 A | 6/1998 | Oppelt et al. |
| 5,762,066 A | 6/1998 | Law et al. |
| 5,766,208 A | 6/1998 | McEwen |
| 5,769,086 A | 6/1998 | Ritchart et al. |
| 5,769,790 A | 6/1998 | Watkins et al. |
| 5,785,705 A | 7/1998 | Baker |
| 5,787,886 A | 8/1998 | Kelly et al. |
| 5,788,636 A | 8/1998 | Curley |
| 5,800,379 A | 9/1998 | Edwards |
| 5,807,308 A | 9/1998 | Edwards |
| 5,810,008 A | 9/1998 | Dekel et al. |
| 5,817,021 A | 10/1998 | Reichenberger |
| 5,817,049 A | 10/1998 | Edwards |
| 5,820,580 A | 10/1998 | Edwards et al. |
| 5,823,962 A | 10/1998 | Schaetzle et al. |
| 5,836,896 A | 11/1998 | Rosenschein |
| 5,840,031 A | 11/1998 | Crowley |
| 5,860,974 A | 1/1999 | Abele |
| 5,868,673 A | 2/1999 | Vesely |
| 5,868,675 A | 2/1999 | Henrion et al. |
| 5,873,828 A | 2/1999 | Fujio et al. |
| 5,873,845 A | 2/1999 | Cline et al. |
| 5,873,902 A | 2/1999 | Sanghvi et al. |
| 5,882,302 A | 3/1999 | Driscoll, Jr. et al. |
| 5,895,356 A | 4/1999 | Andrus et al. |
| 5,897,495 A | 4/1999 | Aida et al. |
| 5,904,681 A | 5/1999 | West, Jr. |
| 5,904,691 A | 5/1999 | Barnett et al. |
| 5,928,169 A | 7/1999 | Schatzle et al. |
| 5,938,600 A | 8/1999 | Van Vaals et al. |
| 5,938,608 A | 8/1999 | Bieger et al. |
| 5,941,889 A | 8/1999 | Cermak |
| 5,944,663 A | 8/1999 | Kuth et al. |
| 5,964,755 A | 10/1999 | Edwards |
| 5,984,881 A | 11/1999 | Ishibashi et al. |
| 5,984,882 A | 11/1999 | Rosenschein et al. |
| 5,993,389 A | 11/1999 | Driscoll, Jr. et al. |
| 6,004,269 A | 12/1999 | Crowley et al. |
| 6,006,127 A | 12/1999 | Van Der Brug et al. |
| 6,007,499 A | 12/1999 | Martin et al. |
| 6,024,718 A | 2/2000 | Chen et al. |
| 6,024,740 A | 2/2000 | Lesh et al. |
| 6,039,689 A | 3/2000 | Lizzi |
| 6,042,556 A | 3/2000 | Beach et al. |
| 6,050,943 A | 4/2000 | Slayton et al. |
| 6,052,611 A | 4/2000 | Yanof et al. |
| 6,064,904 A | 5/2000 | Yanof et al. |
| 6,066,123 A | 5/2000 | Li et al. |
| 6,071,238 A | 6/2000 | Chapelon et al. |
| 6,071,239 A | 6/2000 | Cribbs et al. |
| 6,071,288 A | 6/2000 | Carol et al. |
| 6,083,159 A | 7/2000 | Driscoll, Jr. et al. |
| 6,086,535 A | 7/2000 | Ishibashi et al. |
| 6,088,613 A | 7/2000 | Unger |
| 6,106,517 A | 8/2000 | Zupkas |

| | | |
|---|---|---|
| 6,110,112 A | 8/2000 | Heywang-Koebrunner |
| 6,113,558 A | 9/2000 | Rosenschein et al. |
| 6,117,101 A | 9/2000 | Diederich et al. |
| 6,135,963 A | 10/2000 | Haider |
| 6,135,971 A | 10/2000 | Hutchinson et al. |
| 6,210,330 B1 | 4/2001 | Tepper |
| 6,216,029 B1 | 4/2001 | Paltieli |
| 6,241,725 B1 * | 6/2001 | Cosman .................. 606/41 |
| 6,261,300 B1 | 7/2001 | Carol et al. |
| 6,328,748 B1 | 12/2001 | Hennig |
| 6,352,532 B1 | 3/2002 | Kramer et al. |
| 6,358,245 B1 * | 3/2002 | Edwards et al. ............ 606/34 |
| 6,371,903 B1 | 4/2002 | Blanc et al. |
| 6,379,320 B1 | 4/2002 | Lafon et al. |
| 6,409,722 B1 | 6/2002 | Hoey et al. |
| 6,478,793 B1 * | 11/2002 | Cosman et al. ............ 606/34 |
| 6,491,699 B1 | 12/2002 | Henderson et al. |
| 6,530,922 B2 * | 3/2003 | Cosman et al. ............ 606/34 |
| 6,575,969 B1 * | 6/2003 | Rittman et al. ............ 606/41 |
| 6,580,938 B1 | 6/2003 | Acker |
| 6,599,245 B1 | 7/2003 | Ma et al. |
| 2002/0040220 A1 | 4/2002 | Zvuloni et al. |
| 2002/0042607 A1 | 4/2002 | Palmer et al. |
| 2002/0068930 A1 | 6/2002 | Tasto et al. |
| 2002/0077546 A1 | 6/2002 | Aldefeld et al. |
| 2003/0018266 A1 | 1/2003 | Makin et al. |
| 2003/0220557 A1 | 11/2003 | Cleary et al. |
| 2004/0006336 A1 | 1/2004 | Swanson |
| 2004/0019274 A1 | 1/2004 | Galloway, Jr. et al. |
| 2004/0064148 A1 | 4/2004 | Daum et al. |
| 2004/0092815 A1 | 5/2004 | Schweikard et al. |
| 2004/0143181 A1 | 7/2004 | Damasco et al. |

FOREIGN PATENT DOCUMENTS

| | | |
|---|---|---|
| WO | WO 91/07726 | 5/1991 |
| WO | WO 00/57767 A2 | 10/2000 |
| WO | WO 00/57767 A3 | 10/2000 |
| WO | WO 00/63658 | 10/2000 |
| WO | WO 01/45550 A2 | 6/2001 |
| WO | WO 01/64124 | 9/2001 |
| WO | WO 03/088852 | 10/2003 |
| WO | WO 2004/021898 A1 | 3/2004 |

OTHER PUBLICATIONS

Clare, M.C. et al., MRI Guided Focused Ultrasound Surgery (FUS) of uterine leiomyomas: A Feasibility Study, Workshop on MRI-Guided: Focused Ultrasound Surgery, 2002, Syllabus, International Society for Magnetic Resonance in Medicine.

Vaezy, S. et al., Treatment Of Uterine Fibroid Tumors In A Nude Mouse Model Using High-Intensity Focused Ultrasound, Am J Obstet Gynecol, 2000, pp. 6-11, vol. 183, No. 1.

* cited by examiner nicht # SYSTEM AND METHOD FOR PLANNING TREATMENT OF TISSUE

FIELD OF THE INVENTION

The present invention is generally related to a system for treating tissue with a surgical device inserted into the body and guided by an ultrasound or other imaging device.

BACKGROUND OF THE INVENTION

In one method of treating tumors or lesions in solid organs such as the kidney or the liver, a surgical device such as a radio frequency (RF) ablation probe is placed into the tumor and the tumor cells are destroyed using RF energy. Placement of the ablation probe is accomplished using an imaging system, such as ultrasound imaging. An ultrasound imaging system generates a two-dimensional (2D) image, effectively allowing the doctor or surgeon to view the tissue within the image plane of the ultrasound probe. If the ultrasound probe is positioned such that the axis of the ablation and ultrasound probes are co-aligned, the surgeon can observe the placement of the ablation probe in the tissue on the ultrasound image. However, physical limitations frequently prevent inline placement of the ablation and ultrasound probes. If a tumor is large, more than one placement of the ablation probe may be required to address the tumor volume. In cases where the tumor is larger than can be ablated with one application of RF energy, the ablation probe is repositioned as many times as needed and RF energy is applied at each placement of the ablation probe. For multiple ablation probe applications, the doctor is required to mentally process the 2D ultrasound image to create a plan for ablation probe placement and then to execute the plan. Ten to fifteen minutes may pass between placements of the ablation probe. Placement of the ablation probe outside of the image plane of the ultrasound probe adds to the mental challenge of three-dimensional (3D) planning and makes the procedure difficult. Leaving unablated tumor can result in tumor reoccurrence.

Treatment of the tumor is further complicated by the motion of living tissue. The tumor volume and shape will not change within the time frame of the procedure and may not change in days or even longer; however, motions such as breathing and procedural manipulation will continually alter the location of the tumor within the body. Ablation targeting must be performed on a static image. Due to the changes in the tumor location caused by respiration and the like, a plan generated using a static image cannot be used to determine the trajectory of the surgical device from a fixed targeting position to the target tissue.

There is a need for a method and a device for assisting surgeons in positioning ablation probes and other surgical devices to treat tissue within the body. There is also a need for a method for assisting surgeons in visualizing and planning the insertion of surgical devices. There is a further need for a method of compensating for tumor motion due to patient respiration to increase accuracy in placement of surgical devices and improve treatment of tumors.

SUMMARY OF THE INVENTION

A first expression of an embodiment of the invention provides a method for treating tissue in a body volume with a surgical device. Image data associated with the body volume is collected using an imaging device. An image is created from the imaging data and displayed on a display screen. At least one tissue target in the body volume is selected for treatment. An effective treatment volume of the surgical device is determined. Finally, a treatment modality for treating the tissue target with the surgical device is determined, wherein the treatment modality is made up of at least one target treatment volume.

In a second expression of an embodiment of the invention, the position and orientation of the imaging device, the position of the image and the position and orientation of the surgical device with respect to a reference point are determined. The trajectory of the surgical device with respect to the image on the display screen is indicated. Finally, the surgical device is positioned in the body volume based upon the trajectory, and the tissue target is treated with the surgical device.

A third expression of an embodiment of the invention is identical to the previously described first expression with the following added steps. Information regarding the surgical device is input to determine the treatment volume and the treatment volume is indicated on the display screen.

DETAILED DESCRIPTION OF THE INVENTION

The invention relates to the treating tissue in a patient. For the purposes of describing one embodiment of the present invention, this description will discuss RF ablation of tissue targets using an RF ablation probe guided by ultrasound imaging. This embodiment is merely exemplary in nature and is in no way intended to limit the invention, its application, or uses.

The Surgical Device Guide

Figure 1A:
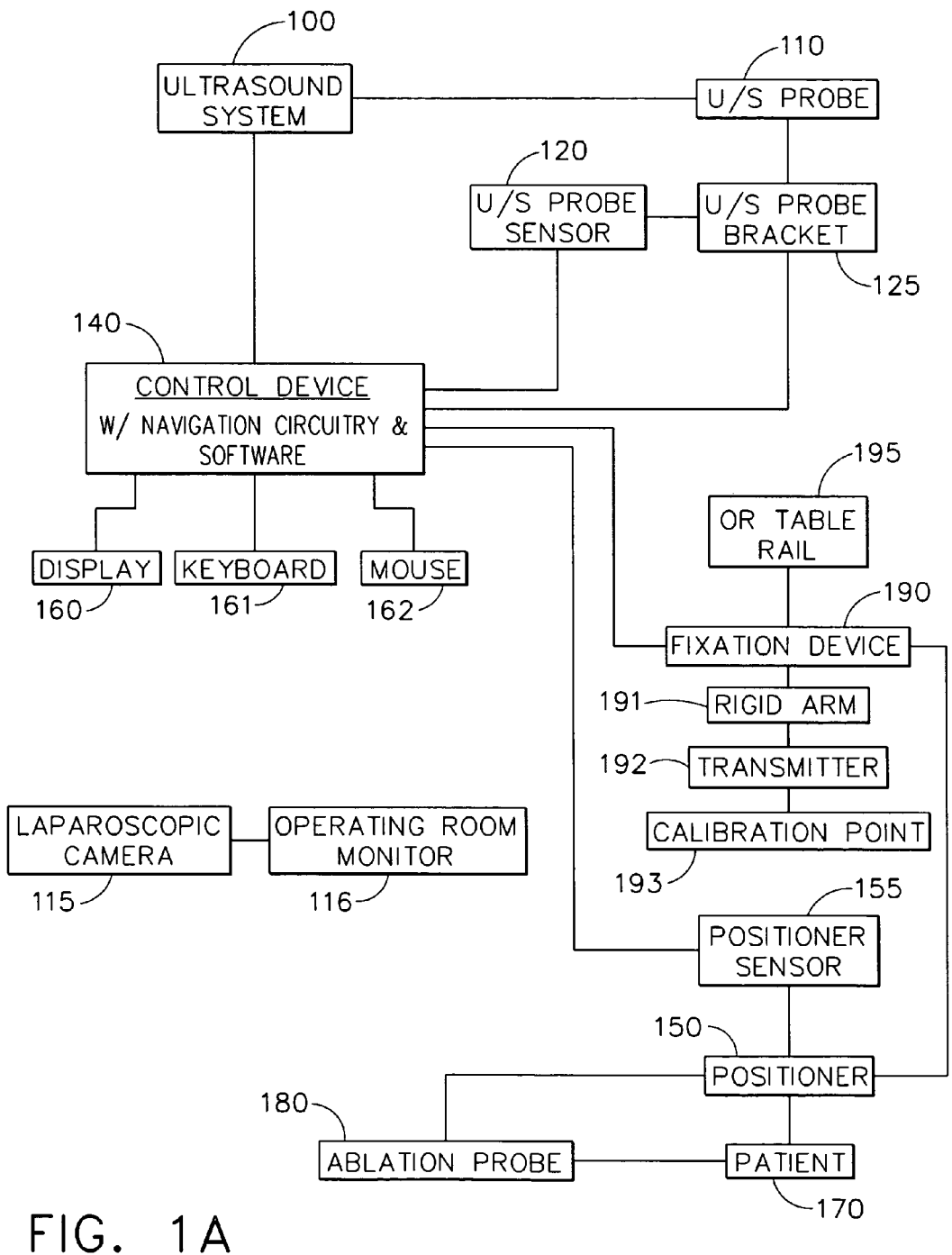
FIG. 1A is a block diagram of the components of the tissue treatment system.
Figure 1B:
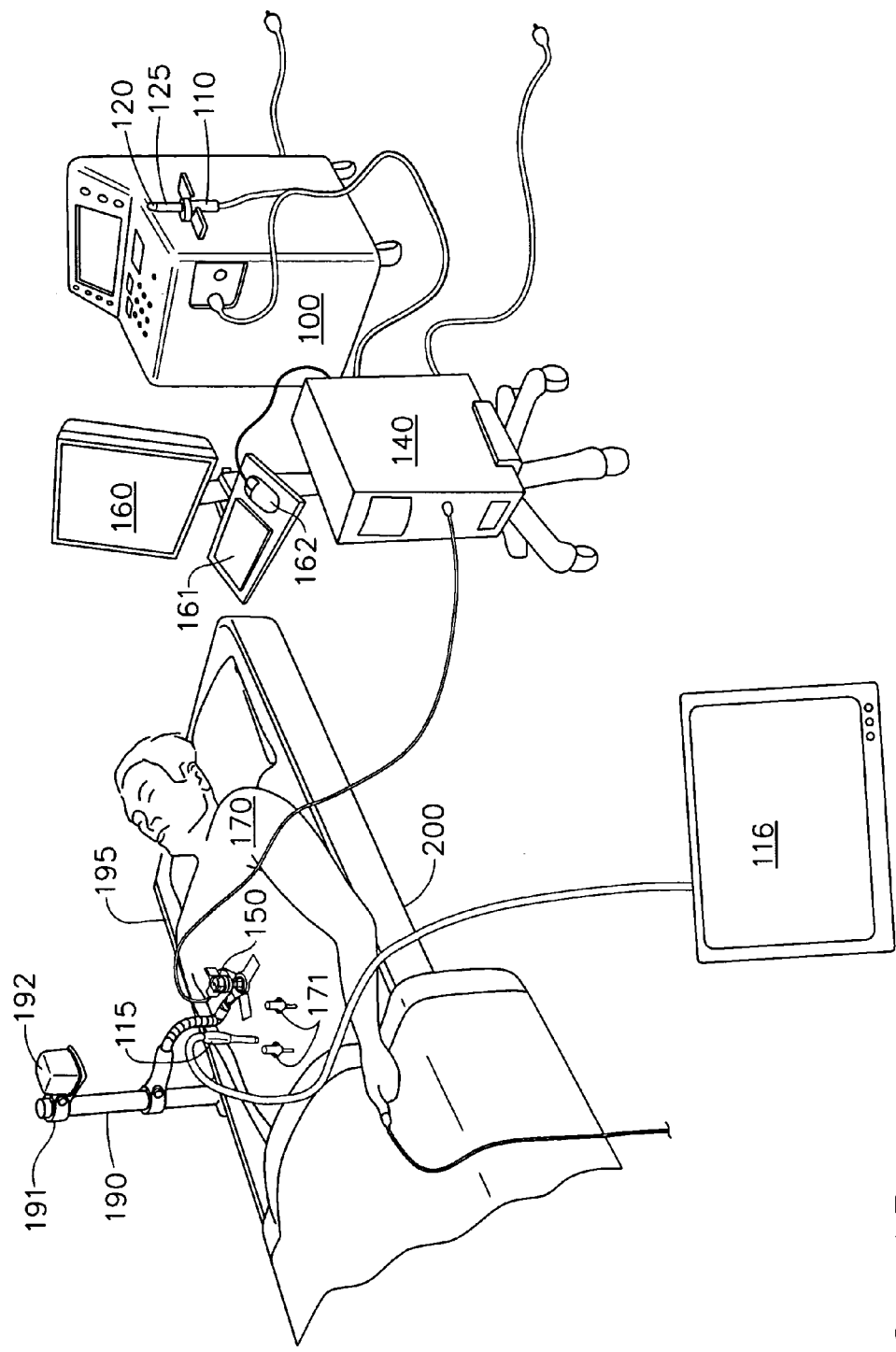
FIG. 1B is an illustration of the tissue treatment system.
Figure 2:
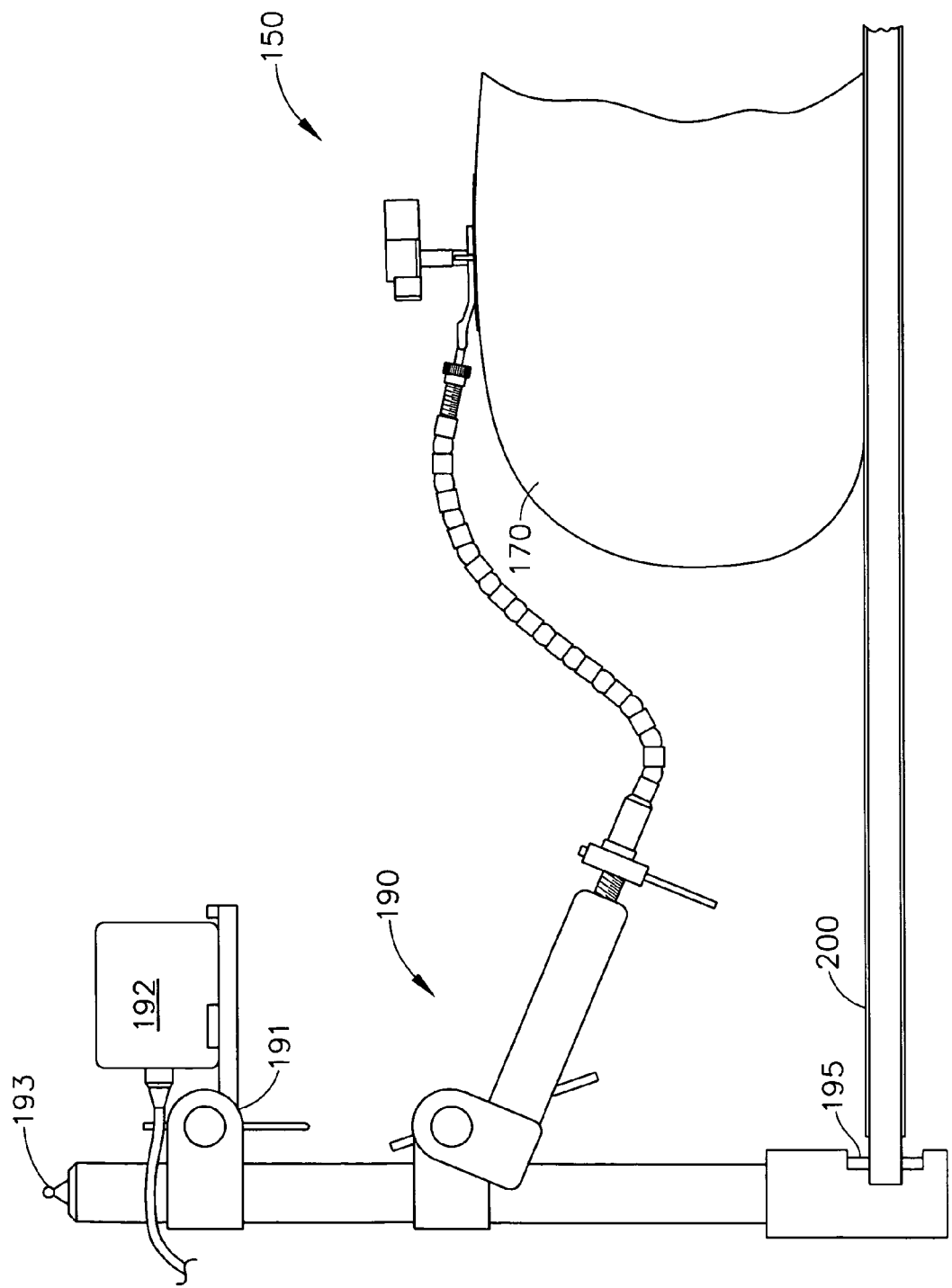
FIG. 2 is a view of the first aspect of the invention illustrating a fixation device.

A first aspect of the invention relates to a surgical device guide, herein referred to as the positioner 150. Referring now to the Figures, FIGS. 1A, 1B, and 2 depict an embodiment of the system components to be used in conjunction with a patient 170 that has been prepared for a laparoscopic procedure. Laparoscopic procedure setup is well known in the prior art. An ultrasound probe bracket 125 with ultrasound probe sensor 120 attaches to a laparoscopic ultrasound probe 110. While the present embodiment utilizes an ultrasound imaging system 100, the invention is not limited to ultrasound devices and encompasses alternative imaging methodologies including, but not limited to, X-ray, computerized tomography (CT), positive electron emission (PET) or magnetic resonance imaging (MRI). Similarly, while the present embodiment utilizes an RF ablation probe 180, the invention encompasses the use of additional surgical devices such as a cryogen ablation probe, a microwave ablation probe, an ultrasound ablation probe, an ultrasound transducer, a heated element, and the like. The ultrasound system 100 generates image data that is transmitted to a control device 140. The ultrasound probe sensor 120 provides position and orientation information to the control device 140 to assist in the "stacking" of the 2D ultrasound images to form a simulated 3D volume.

The control device 140 contains navigation circuitry and software to process the ultrasound 2D images generated by ultrasound probe 110 to form the simulated 3D image and the location information provided by the ultrasound probe sensor 120. The control device 140, as used herein, may consist of a singular device or as multiple devices working together. One skilled in the art will appreciate that the functions of the control device 140 may be broken down over several components. A display screen 160, keyboard 161 and mouse 162 may be connected to the control device 140. Alternative embodiments may use other input devices such as track balls, touch screens, styluses or the like. The control device 140 is mounted on a mobile cart 210 which supports keyboard 161 and mouse 162 input devices as well as the display screen 160. Images generated by the system are displayed on the display screen 160.

The positioner 150 is a surgical device guide and includes a positioner sensor 155 which is also connected to the control device 140. During the procedure, the patient 170 lies on an operating table 200 and the positioner 150 is placed in contact with the patient 170. The ablation probe 180 is inserted into the patient 170 through the positioner 150. The positioner 150 is given additional stability by a fixation device 190 that attaches to an operating room table rail 195. The fixation device 190 depicted in FIG. 2 is available in the Bookwalter Endoscopic Instrument Kit commercially available from Codman, Inc. of Raynham, Mass. Alternative embodiments may include other fixation devices or adhesives to stabilize the location of the positioner 150 with respect to the patient 170.

In one embodiment, the fixation device 190 has a rigid arm 191 that supports a transmitter 192. In an alternative embodiment, the transmitter 192 may be attached to the wall or ceiling of the room, or any other fixed location. The signal from the transmitter 192 is picked up by both the ultrasound probe sensor 120 and positioner sensor 155 and serves as a reference point for the system. The fixation device may also include a fixed calibration point 193 used to calibrate the positioner 150.

In one embodiment, orientation and position of the positioner 150 and the ultrasound probe 110 are determined based upon magnetic field sensors, such as the sensors described in U.S. Pat. No. 4,945,305 to Blood, the disclosure of which is incorporated herein by reference. The system includes a magnetic transmitter 192 mounted on the fixation device 190, a magnetic positioner sensor 155 attached to the positioner 150, and a magnetic ultrasound probe sensor 120 attached to the ultrasound probe 110. The control device 140 is capable of performing the calculations necessary to determine the location of the positioner 150 with respect to the images generated by the ultrasound probe 110. There are several possible methods of determining the position and orientation of the positioner 150 and ultrasound probe 110. An alternative embodiment utilizes optical sensors attached to the positioner 150 and ultrasound probe 110 to detect their position and orientation. A laparoscopic camera 115 may be present and connected to the control device 140 to enable side-by-side viewing of the camera 115 with other displays generated by the control device 140. Alternatively, the laparoscopic camera may be connected to an independent operating room monitor 116.

Figure 3A:
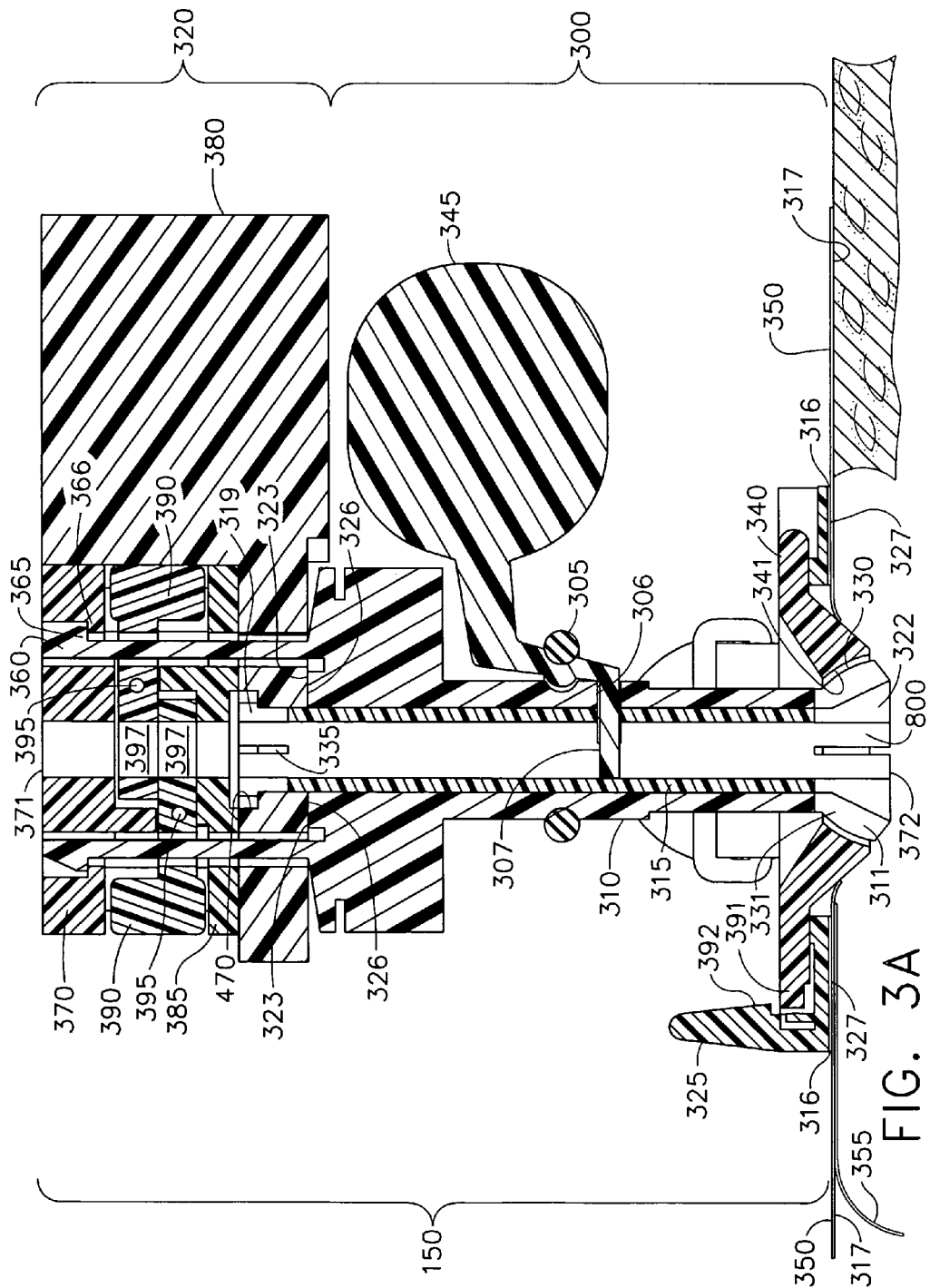
FIG. 3A is a cross section of a first embodiment of a first aspect of the invention illustrating the surgical device guide.
Figure 3B:
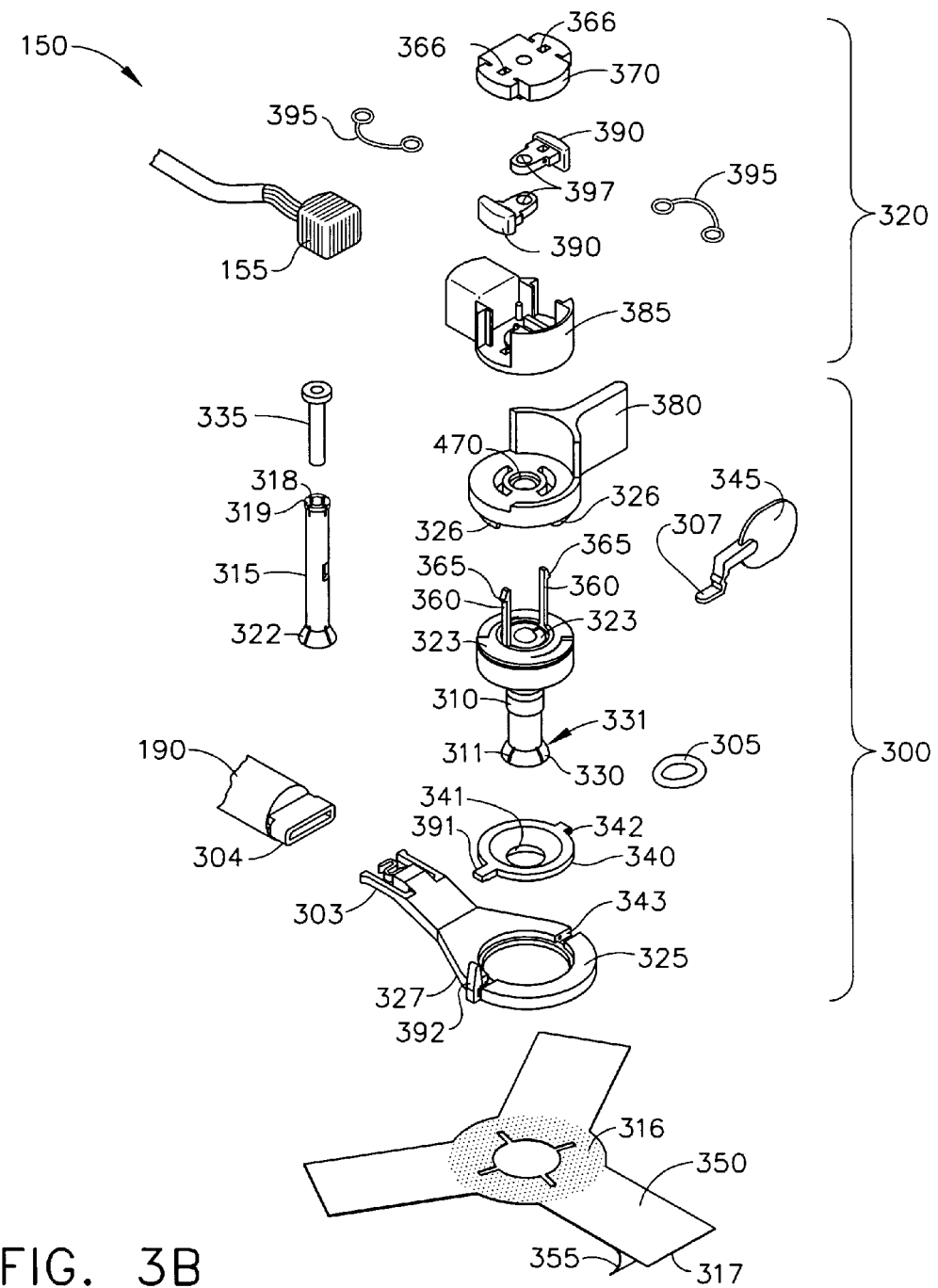
FIG. 3B is an exploded view of a first embodiment of a first aspect of the invention.

Referring now to FIGS. 3A and 3B, in a second embodiment of a first aspect of the invention, the positioner 150 consists of a stem assembly 300 and a depth stop assembly 320. Within the stem assembly is an outer stem 310 that includes a semispherical portion 331. Semispherical, as used herein, means having the shape of a portion of a sphere. The semispherical portion 331 has a stem radius 330 with slots 311 that enable the stem radius 330 to nestle into a corresponding frame radius 341 of frame 340. The stem radius 330 and the frame radius 341 function similarly to a ball joint, allowing the outer stem 310 to rotate with respect to the frame 340. In an alternative embodiment, the outer stem 310 may be connected to the frame 340 by a ball joint.

An inner stem 315 including a stem flare feature 322 that mates with the inside surface of the semispherical portion of the outer stem 331 is positioned within the outer stem 310. The inner stem 315 has a channel 800 into which a needle-like surgical device, such as an RF ablation probe, a biopsy needle or the like may be inserted. The surgical device may be inserted into the positioner 150 through the entry point 371, pass through the channel 800 and exit the positioner 150 at the exit point 372. The channel 800 may be cylindrical in shape.

Alternatively, the channel 800 may be multi-sided or triangular such that the sides of the channel 800 securely grip the surgical device. The proximal end of the inner stem 315 includes notches 318 that enable the stem head 319 to snap into a recess 470 in knob 380. The knob 380 has a ramp surface 326 that engages the outer stem ramp surface 323. Grasping the knob 380 and rotating it to one side draws the inner stem 315 through the outer stem and, consequently, draws the semispherical portion 331 of the outer stem into the mating frame radius 341. The slots 311 allows the stem radius 330 to expand and reactive forces fix the angular position of the outer stem 310 in the chosen orientation, locking the trajectory of any inserted surgical device. Trajectory, as used herein, refers to the path of the surgical device into the body of the patient.

In one embodiment, the frame 340 is attached to a holder 325 by a hinged joint. The frame 340 includes a hinge pin 342 feature that mates with a hinge recess 343 of the holder 325. A snap lever 391 engages a snap catch 392 to secure the frame 340 within the holder 325. Disengaging the snap lever 391 and the snap catch 392 allows the frame 340 to be rotated out of the holder 325, permitting the surgeon to access the skin of the patient 170. The holder 325 has a bottom surface 327 that bears against the skin of the patient 170. The center of the stem radius 330 is located on or marginally below the bottom surface 327, putting the center of stem radius 330 in contact with patient 170. In this embodiment, the center of angular rotation of the stem radius 330 is at or near the skin of the patient 170 without significant skin deformation, due to the semispherical shape of the stem radius 330. Placing the center of rotation at or near the surface of the skin maximizes the range of angular motion through the incision in the skin and minimizes the size of the incision required. In one embodiment, the holder 325 has a clip end 303 which may be attached to the mating receptacle 304 of a fixation device 190. The holder 325 may also utilize a flexible stabilizer 350 to fix the position of the holder 325 with respect to the patient 170. A flexible stabilizer 350 has a ring adhesive 316 that enables it to attach to the flat area 327 of the holder 325 and a patient adhesive 317 which attaches to the patient 170. The patient adhesive 317 is covered by a peelable cover 355 to prevent the flexible stabilizer 350 from adhering prior to final placement of the positioner 150 on the patient 170.

The depth stop assembly 320 is seated on top of the knob 380 and is attached to the outer stem 310 by deflection fingers 360. The depth stop assembly 320 consists of a sensor frame 385, an end disc 370, two button catches 390, and their respective elastic bands 395. The shelves 365 of the deflection fingers engage a lip 366 of the end disc 370. The depth stop 320 utilizes a positioner sensor 155 embedded in the sensor frame 385 to communicate the positioner 150 location and orientation to the control device 140. The sensor frame 385 houses the button catches 390 and their respective elastic bands 395. Squeezing the button catches 390 bends the deflection fingers 360 and releases the depth stop assembly 320 from the outer stem 310. The end disc 370 covers the depth stop assembly 320 and is fixed in place.

In one embodiment, a movable shutter 345 is attached to the outer stem 310 and prevents surgical devices from passing through the channel 800 of the positioner 150. The shutter 345 incorporates a shutter stop 307, which passes through the window access port 306 and projects into the channel 800. The shutter 345 is held in place by an elastic ring 305, which allows the shutter 345 to pivot. Surgical devices inserted in the positioner 150 rest upon the shutter stop 307 at a known, fixed reference position. The shutter 345 is pulled, but not removed, from the window access port 306 to remove the shutter stop 307 from the channel 800 and allow surgical devices to pass through the positioner 150. In an alternative embodiment, the shutter 345 may be attached to the outer stem 310 by a hinged joint biased by a spring. Pressure on the shutter 345 causes it to pivot and removes the shutter stop 307 from the channel 800. An insert 335 may be placed in the channel 800 to accommodate surgical devices of different diameters.

Figure 4A:
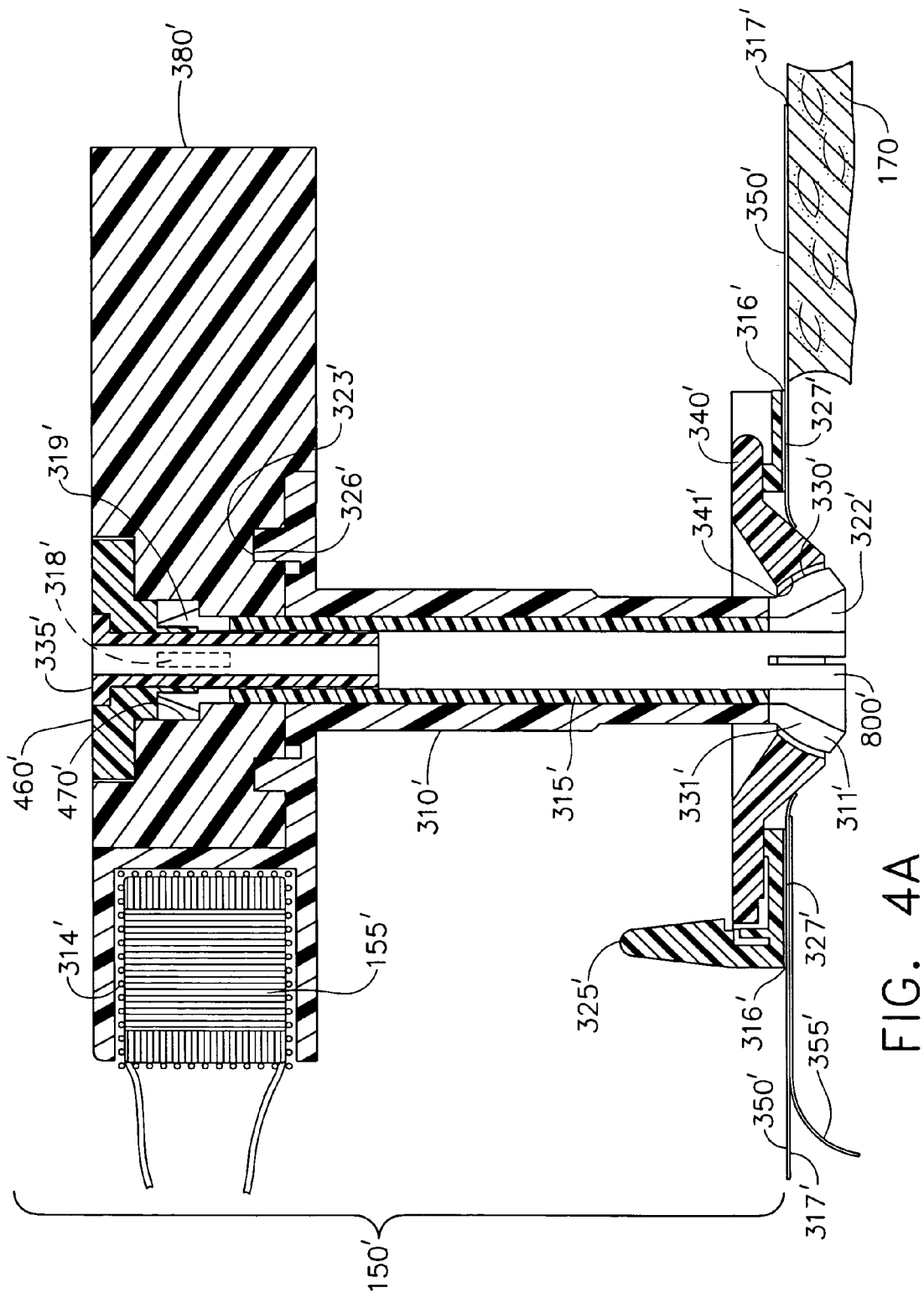
FIG. 4A is a cross section of a second embodiment of a first aspect of the invention.
Figure 4B:
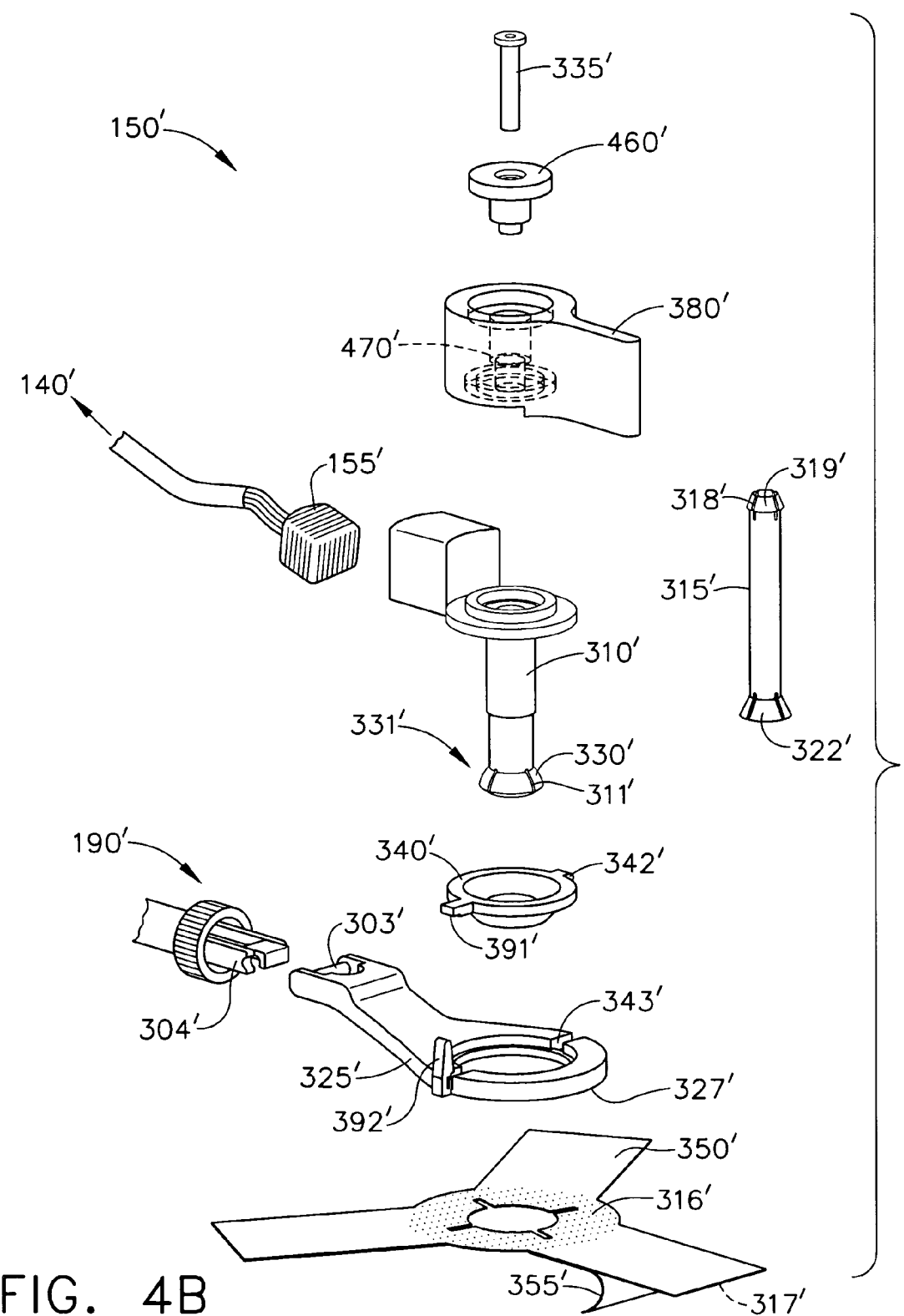
FIG. 4B is an exploded view of a second embodiment of a first aspect of the invention.

Referring now to FIGS. 4A and 4B, a second embodiment of the first aspect of the invention, the positioner 150' includes a positioner sensor 155' housed in the outer stem 310', held in place with potted epoxy 314' and connected to a control device 140'. This alternative embodiment does not include a depth stop assembly 320 or a shutter 345 as described in the previous embodiment. However, as in the previous embodiment, the proximal end of the inner stem 315' has notches 318' that enable the stem head 319' to snap into a recess 470' of knob 380'. In the present embodiment a cap 460' inserts into stem head 319' to keep it securely in place. An insert 335' may be placed in the channel 800' to accommodate surgical devices of different diameters.

As in the first embodiment of the first aspect of the invention, the knob 380' has a ramp surface 326' that engages an outer stem ramp surface 323'. Grasping the knob 380' and rotating it to one side draws the inner stem 315' through the outer stem and, consequently, draws a semispherical portion 331' of the outer stem into a mating frame radius 341' of a frame 340'. Slots 311' allows the stem radius 330' of a stem flare feature 322' of the outer stem 310' to expand and reactive forces fix the angular position of the outer stem 310' in the chosen orientation, locking the trajectory of any inserted surgical device.

In one embodiment, the frame 340' is attached to a holder 325' by hinge pin 342' feature that mates with a hinge recess 343' of a holder 325'. A snap lever 391' engages a snap catch 392' to secure the frame 340' within the holder 325'. The holder 325' has a clip end 303' which may be attached to the mating receptacle 304' of a fixation device 190' to hold the positioner 150' in place. The holder 325' may also utilize a flexible stabilizer 350' to fix the position of the holder 325' with respect to the patient 170'. The flexible stabilizer 350' has a ring adhesive 316' that enables it to attach to a flat area 327' on the holder 325' and a patient adhesive 317' which attaches to the patient 170'. The patient adhesive 317' is covered by a peelable cover 355' to prevent the flexible stabilizer 350' from adhering prior to final placement of the positioner 150' on the patient 170'.

Figure 5:
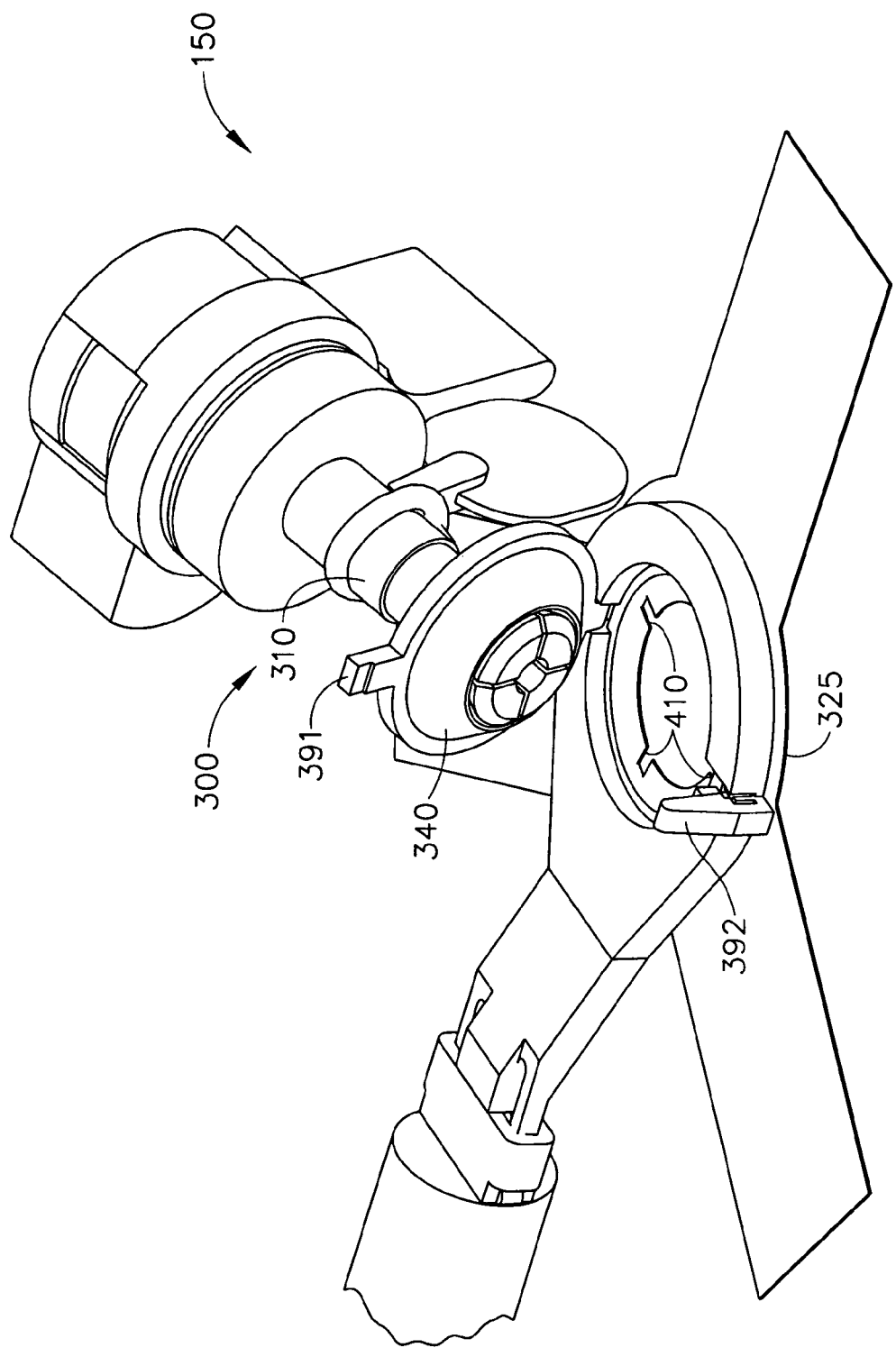
FIG. 5 is a perspective view of a first aspect of the invention depicting the stem assembly rotated to expose the skin of the patient.

Referring now to FIG. 5, in one embodiment, the stem assembly 300 of the positioner may be rotated to expose the patient's skin by disengaging snap lever 391 from snap catch 392. Four slots 410 within the holder 325 act as skin nick guides, enabling a scalpel to create a transdermal incision between the slots for easy insertion of the surgical device through the skin. Re-engaging the snap lever 391 and snap catch 392 returns the outer stem 310 to its fixed position within the positioner 150. In an alternative embodiment the stem assembly 300 may be connected to the holder 325 using multiple snap catches rather than a hinged joint, so that the stem assembly 300 may be removed from the holder 325 to expose the skin. In yet another alternative embodiment, a lance may be inserted through the channel 800 to nick the skin without removing the stem assembly 300 from the holder 325.

Figure 6A:
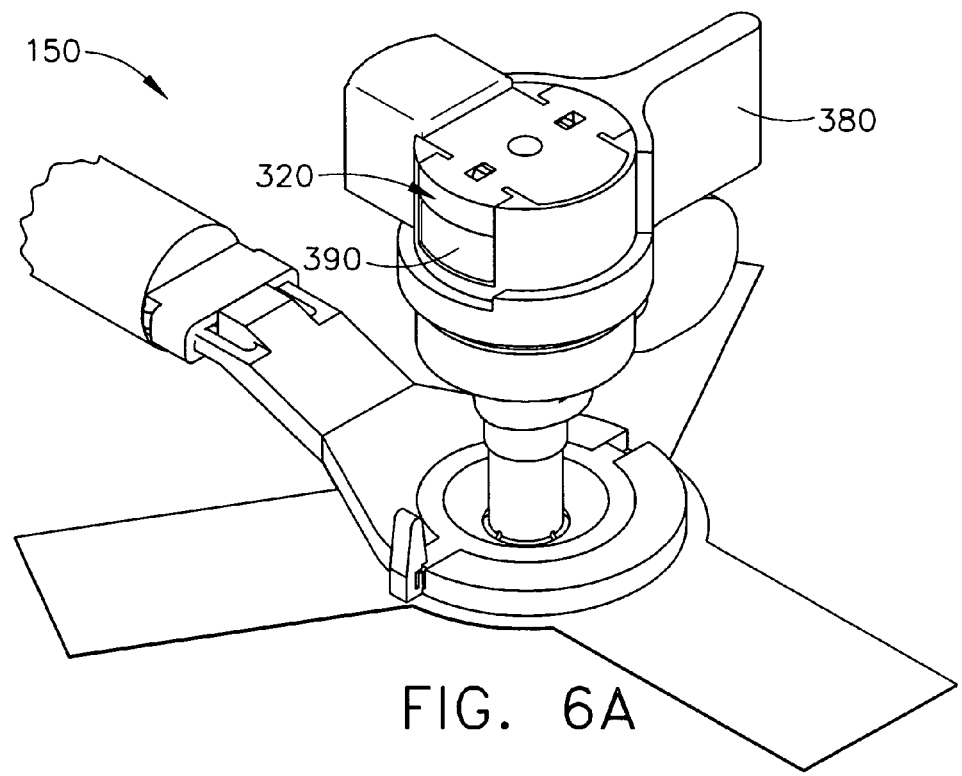
FIG. 6A is a perspective view of a first embodiment of a first aspect of the invention depicting the positioner in an unlocked position.
Figure 6B:
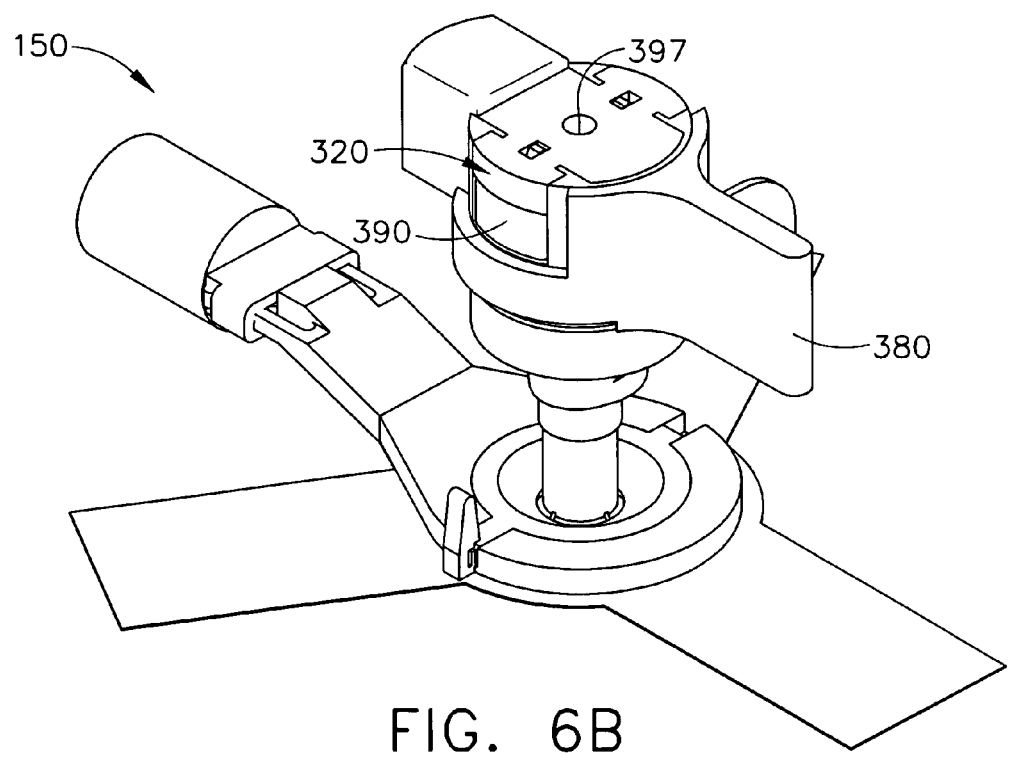
FIG. 6B is a perspective view of a first embodiment of a first aspect of the invention depicting the positioner in a locked position.

Referring now to FIGS. 6A and 6B, in one embodiment, the depth stop assembly 320 includes button catches 390 which allow the depth stop assembly 320 to be removed from the outer stem 310. When the positioner 150 is in an unlocked position, the knob 380 covers one of the button catches 390 preventing the depth stop 320 from being removed from the outer stem 310. Rotating the knob 380 to the locked position exposes the second button catch 390. Squeezing the button catches 390 aligns the through holes 397 and allows the depth stop assembly 320 to be removed from the outer stem 310.

Figure 6C:
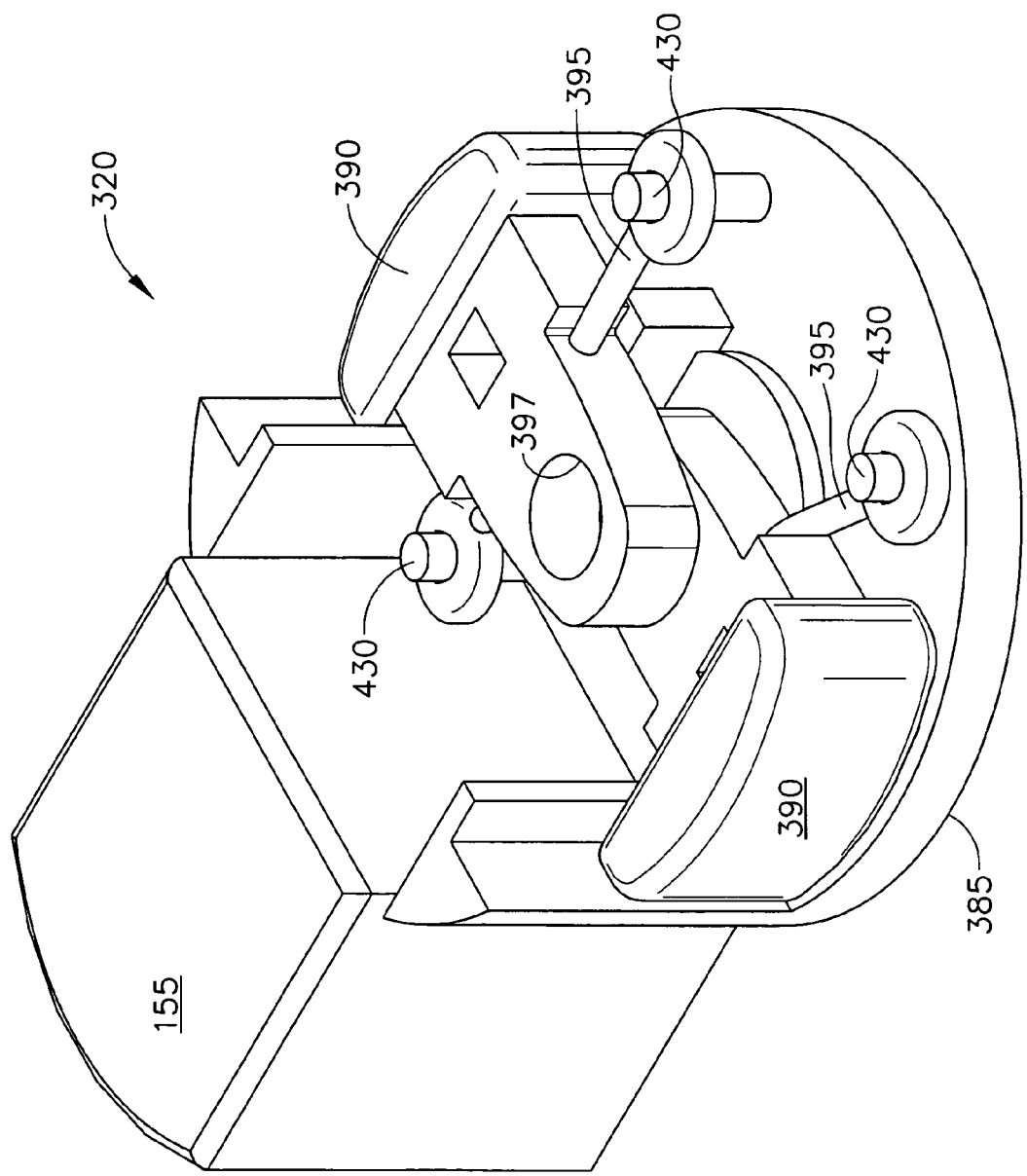
FIG. 6C is a perspective view a first aspect of the invention depicting the depth stop assembly.
Figure 6D:
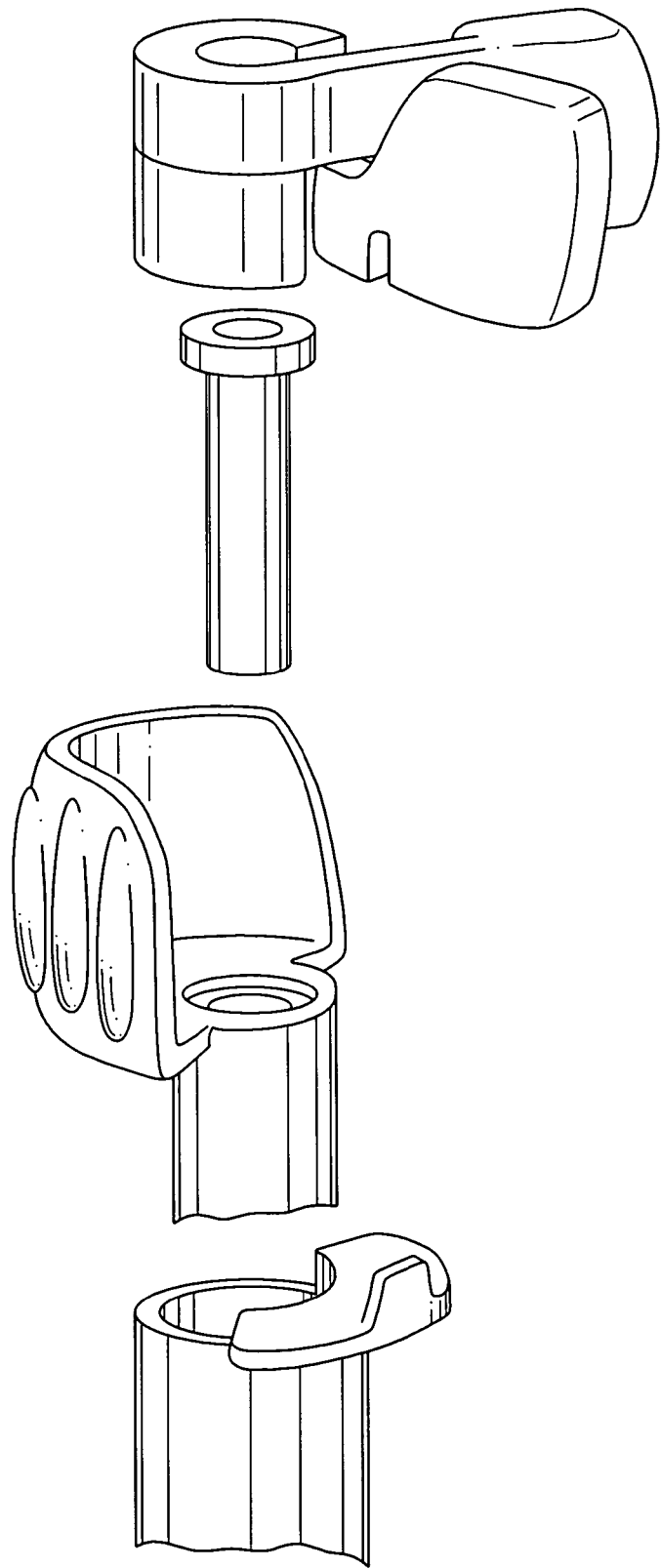
FIG. 6D is an exploded view of a first aspect of the invention depicting an alternative embodiment of the depth stop assembly.
Figure 6E:
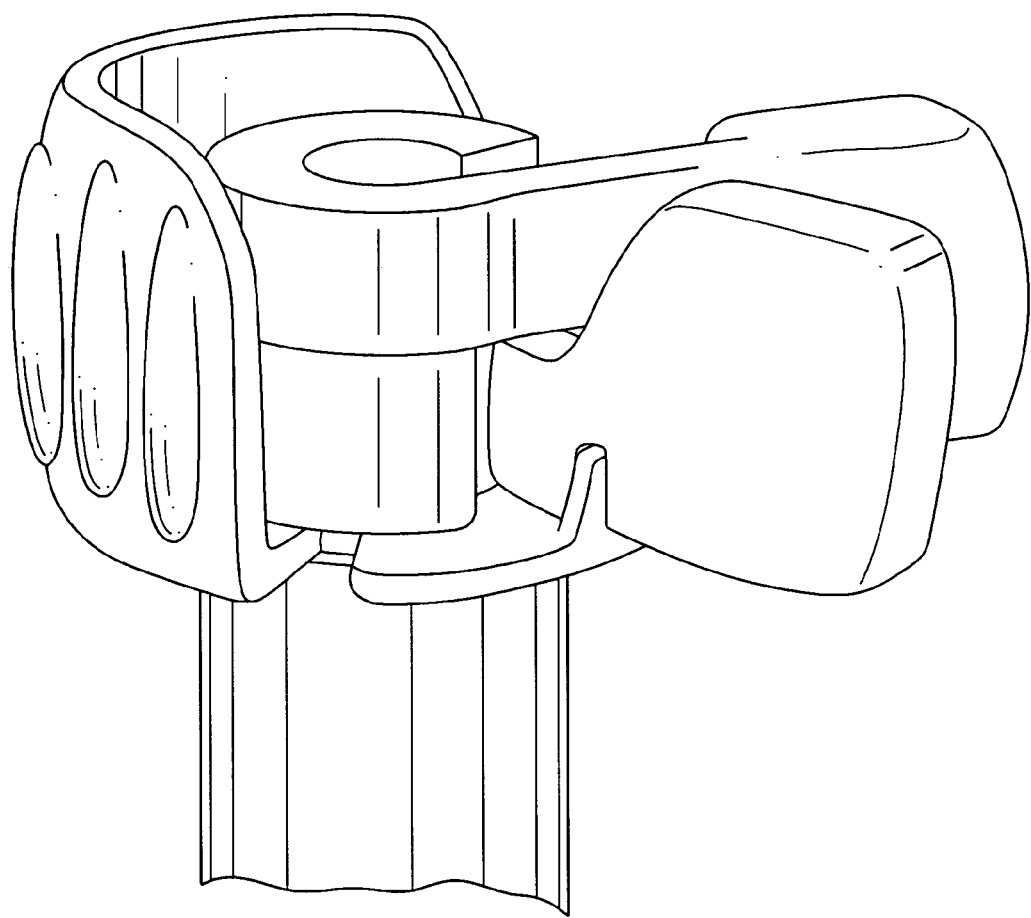
FIG. 6E is a perspective view of a first aspect of the invention depicting an alternative embodiment of the depth stop assembly.

Referring now to FIGS. 6C, 6D and 6E, in one embodiment, the button catches are biased by elastic bands 395 attached to posts 430 of the sensor frame 385. Squeezing the button catches 390 stretches the elastic bands 395 and aligns the through holes 397. An alternative embodiment of the depth stop 320 construction using a clamp without a positioner sensor 155 is depicted in FIGS. 6D and 6E.

Referring now to FIGS. 7A, 7B, 7C and 7D, when the button catches 390 are squeezed the through holes 397 align. An ablation probe 180 may be inserted into the channel 800 through the through holes 397 until it rests against the shutter stop 307 at a known, fixed, reference position. Squeezing the button catches 390 moves the deflection fingers, allowing the depth stop 320 to be removed from the outer stem 310 and positioned on the ablation probe 180. When the button catches 390 are released, the through holes 397 become misaligned and grip the ablation probe 180. The through holes 397 act as a clamp, fixing the position of the depth stop 320 on the ablation probe 180.

Figure 8A:
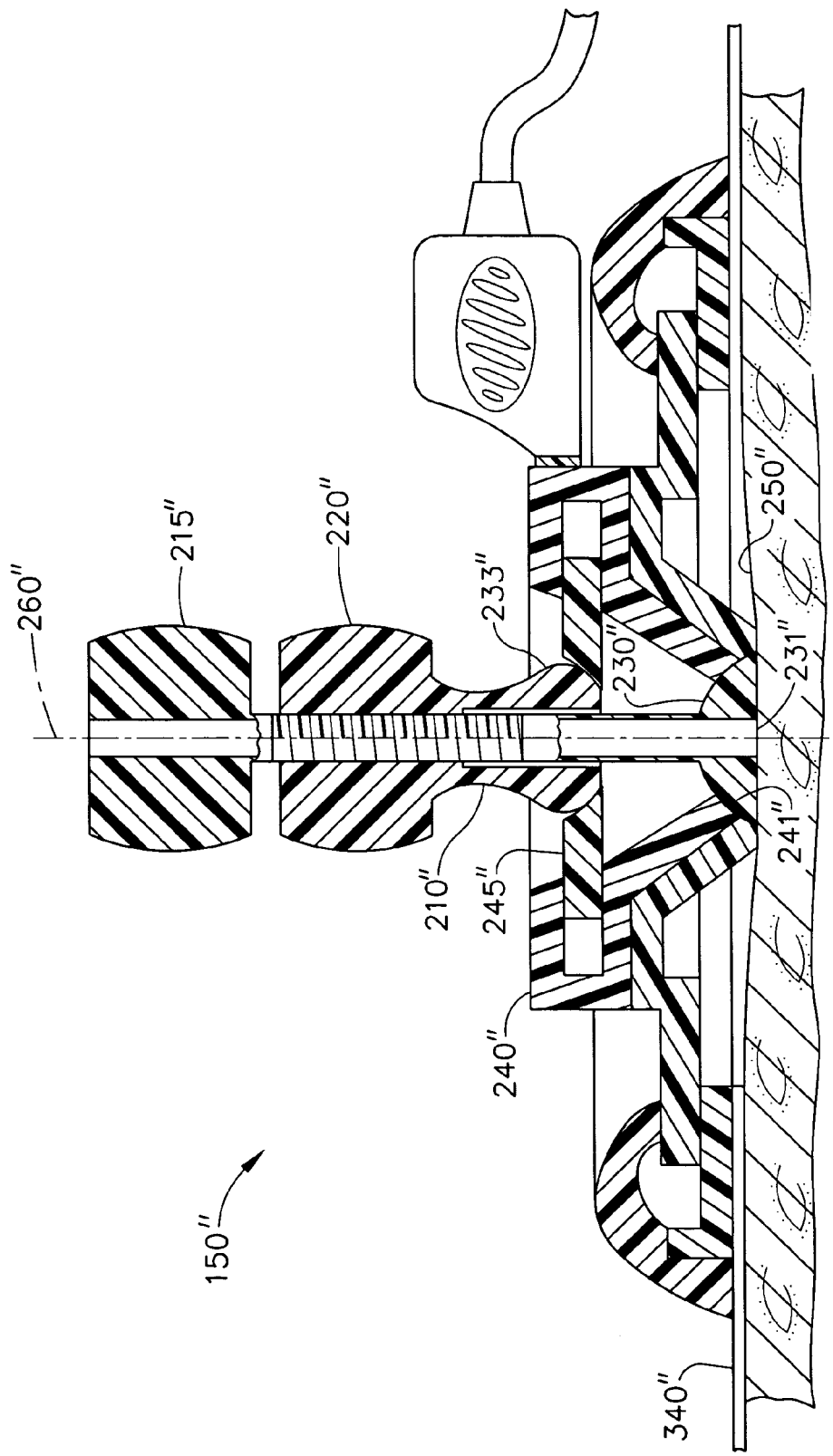
FIG. 8A is a cross section of a third embodiment of the first aspect of the invention.
Figure 8B:
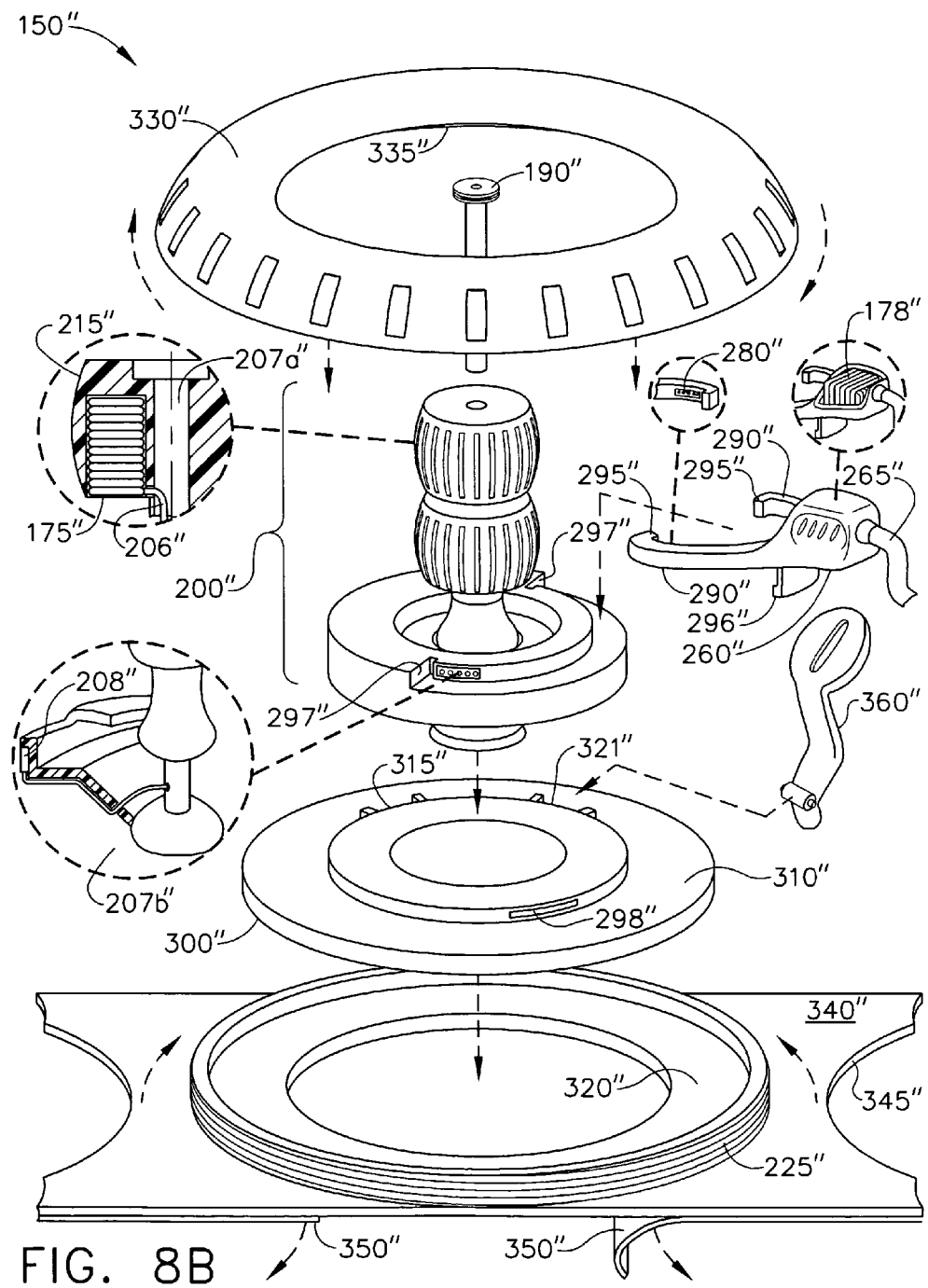
FIG. 8B is an exploded view of a third embodiment of a first aspect of the invention.

Referring now to FIGS. 8A and 8B, a third embodiment of a first aspect of the invention includes a sliding disk 310" which allows the surgeon to adjust the insertion point after the holder 325 has adhered to the patient. As used herein, insertion point is the point on the skin of the patient where the ablation probe is inserted. In the embodiment depicted in FIGS. 8A and 8B, the stem assembly 200" has a single stem 210" with a semispherical portion 231" at its distal end. The semispherical portion 231" has a stem radius 230" that nestles into a corresponding frame radius 241" of a frame 240" and a bottom surface that bears against patient 250". The stem radius 230" and the frame radius 241" function similarly to a ball joint, allowing the stem 210" to rotate with respect to the frame 240". Therefore, the center of angular rotation of the stem radius 230" is at or near the skin of the patient 250" without significant skin deformation, maximizing the range of motion through a small incision in the skin of the patient 250". A locking knob 220" is attached to the stem 210" by a threaded surface. The locking knob 220" has a locking knob radius 233" that bears on the disk feature 245". The disk feature 245", in turn, bears on the frame 240".

The axis 260" of stem 210" determines the trajectory of positioner 150". Grasping the knob 215" and moving it in one direction will cause stem 210" to pivot about the center of stem radius 230", changing the trajectory of the positioner 150' and any inserted surgical device. The bottom surface on semispherical portion 231" will rock gently on the skin of patient 250", allowing the center of stem radius 230" to maintain contact with the patient. The stem radius 230" will slide against the abutting corresponding radius on frame 240". Additionally, the locking knob radius 233" will slide against the adjacent radius on the disc feature 245", moving disk feature 245 within the slot in frame 240".

The locking knob 220" may be used to lock stem 210" into a fixed position after the trajectory is planned. Rotating locking knob 220" in one direction will force the locking knob radius 233" against its mating radius in the disk feature 245" and will pull semispherical portion 231" against frame 240" at the point where radius stem 230" abuts frame 240". The reactive forces will lock the stem 210" into the chosen position.

The sliding disk 310" allows the insertion point of the surgical device to be adjusted after the base 320" is fixed in position. Frame 240" is attached to the platform 300" by a hinge joint. The platform 300' has a sliding disk 310' that sits upon holder 320". The insertion point may be shifted by moving the sliding disk 310" upon the holder 320". A ring 330" includes threaded surface 335" that interfaces with threaded surface 225" of the holder 320". Rotating the ring 330" in one direction will force the edge of the ring 330" against the sliding disk 310". The frictional forces from the ring 330" and the holder 320" will fix the position of the sliding disk 310".

In this alternative embodiment, the positioner sensor 175" is embedded into the knob portion 215" of stem 210". The positioner sensor 175" wires enter stem slot 207a", traverse the inner slot 206" and exit at stem slot 207b". The wires of positioner sensor 175" then pass through the frame 240" and terminate on an edge card 208". A positioner transmitter 178" is embedded in the clamp arm 260" which will be attached to the frame 240". The wires of positioner transmitter 178" are encased within cable 265". The clamp arm 260" includes an embedded edge card 280" in one of the flex members 290" that mates with the edge card 208" in the frame 240". Wires from the edge card 208" in the frame 240" connect with the wires of the edge card 280" embedded in the clamp arm 260". The tips 295" of the flex members 290" snap into grooves 297" of the frame 240". A tab 296" of the clamp arm 260" catches the recess 298" in platform 300" to hold the clamp arm 260" in place.

The positioner 150" includes a skin nick guide 330" which assists the surgeon in making a transdermal incision aligned with the center of the stem assembly 200". The platform 300" includes a stem hinge 315" that allows the stem assembly 200" to be rotated out of the center of the platform 300". The platform 300" includes a skin nick guide hinge 321" that enables the skin nick guide 360" to rotate into the center of the platform 300", such that the slot in the skin nick guide 330" is aligned with the center of the aperture in the platform 300". When not in use, the skin nick guide 330" is rotated out of the platform 300". The holder 320" includes an adhesive 340" to attach the positioner 150" to the patient 120". The adhesive 340" has a peelable cover 350" to prevent the adhesive 340" from adhering prior to final placement of the positioner 150". An insert 190" may be placed in the stem 210" to accommodate surgical devices of different diameters.

Figure 9A:
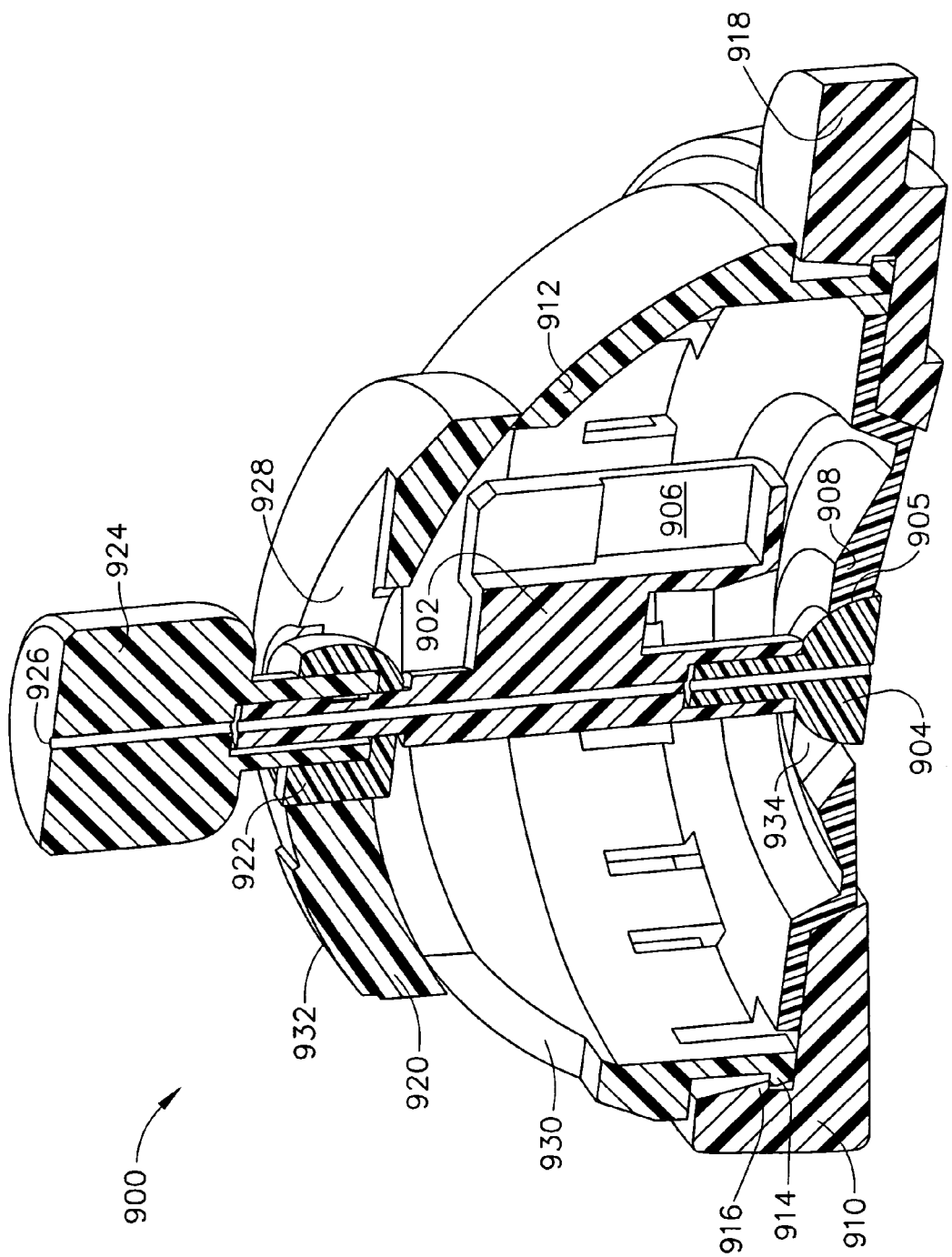
FIG. 9A is a cross section of a fourth embodiment of the first aspect of the invention.
Figure 9B:
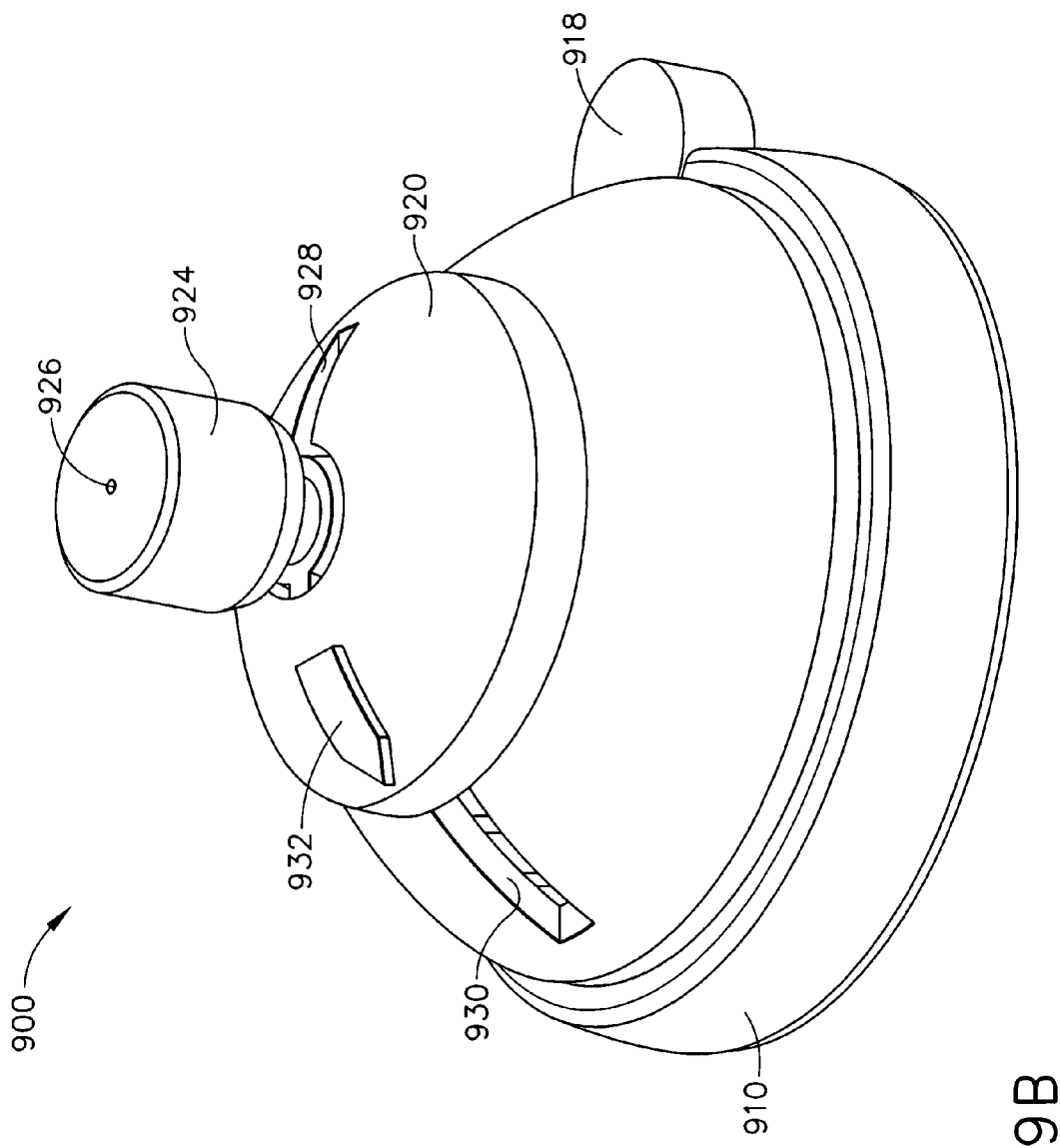
FIG. 9B is perspective view of the fourth embodiment of the first aspect of the invention.

Referring now to FIGS. 9A and 9B, in a fourth embodiment of a first aspect of the present invention, positioner 900 utilizes domed structure to facilitate changes in the trajectory of the surgical device. The positioner 900 includes a stem 902 with a stem flare feature 904 at its distal end. The stem flare feature 904 nestles into a corresponding frame radius 905 of a frame 908 and functions similarly to a ball joint. The stem 902 has a channel 926 for insertion of a surgical device. The stem 902 includes a sensor arm 906 which houses the positioner sensor (not shown). The frame 908 is seated within the holder 910 and attached to the lower dome 912. The lower dome 912 has fingers 914 which engage the lip 916 of the holder 910 to attach the lower dome 912 to the holder 910. The snap catch 918 is pivotally mounted on the holder 910. Depressing the snap catch 918 releases one of the fingers 914 of the lower dome 912 and allows the lower dome 912 to be removed from the holder 910. Removal of the lower dome 912 from the holder 910, also removes the frame 908 from the holder 910 and allows the surgeon to access the skin of the patient even after the holder 910 is fixed in place. The holder 910 may be secured to the patient using a flexible stabilizer (not shown) or, in an alternative embodiment, the holder 910 may include a clip end capable of being attached to a fixation device. An upper dome 920 rests on the lower dome 912. Wires from the positioner sensor (not shown) seated in the sensor arm 906 may pass through a slot 928 in the upper dome 920 to connect the positioner sensor to the control device. The stem 902 passes through a collar 922 within the upper dome 920. A knob 924 including a threaded surface engages a threaded surface on the stem 902. The knob 924 includes the channel 926 into which a surgical device may be inserted The configuration of the upper dome 920 and lower dome 912 allows the surgeon to manipulate the trajectory of the positioner 900. The upper dome 920 slides over the surface of the lower dome 912, allowing the stem 902 to rotate. The surgeon may change the angle of insertion by grasping and moving the knob 924, thereby changing the angle of the stem 902 and the channel 926 into which the surgical device will be inserted. The angle of insertion is limited by contact between the collar 922 surrounding the stem 902 and the top edge of the lower dome 912. A slot 930 in the lower dome 912 and a matching frame slot 934 in the frame radius 905 increase the range of the angle of insertion and therefore the trajectory. The collar 922 may be inserted in the slot 930 to increase the angle of insertion. When the collar 922 is inserted in the slot 930 in the lower dome 912, the stem 902 is inserted into the matching frame slot 934 in the frame radius 905. An arrow 932 on the upper dome 920 indicates when the upper dome 920 is aligned such that the collar 922 may be inserted into the slot 930 in the lower dome 912 without interference due to the sensor arm 906. The lower dome 912 may be rotated three hundred and sixty degrees within the holder 910, thereby allowing the surgeon to reposition the slot 930 and the frame slot 934 as needed.

Once a preferred trajectory is established, the surgeon may lock the trajectory of the positioner 900. The trajectory may be locked by grasping and turning the knob 924. Rotating the knob 924 in one direction will draw the stem 902 up through the collar 922, drawing the stem flare feature 904 of the stem 902 into the mating frame radius 905. At the same time, the bottom of the knob 924 will press down on the collar 922. Reactive forces fix the angular position of the stem 902 in the chosen orientation, locking the trajectory of a surgical device inserted in the channel 926.

In a fifth embodiment of the first aspect of the present invention, the depth stop assembly 320 may be used independently from the remainder of the positioner 150. The depth stop 320 may be used with any surgical device of a fixed geometry to control insertion of the surgical device within a patient 170. First, the depth stop assembly, including the positioner sensor 155, is associated with an insertion point. Next, the depth stop assembly is positioned on a surgical device that has a known, fixed geometry. The tip of the surgical device must be located at a known reference point relative to the depth stop assembly. Using the known geometry of the surgical device and the position and orientation of the reference point and depth stop, the control device 140 is able to calculate the position of the tip of the surgical device upon insertion into the patient 170. In the Figures, the depth stop is illustrated in conjunction with a needle-like surgical device. However, the depth stop assembly may be used with any surgical device of a fixed geometry, if the geometry is known and input into the control device 140.

Method for Mapping Treatment Targets onto Tissue

Figure 10A:
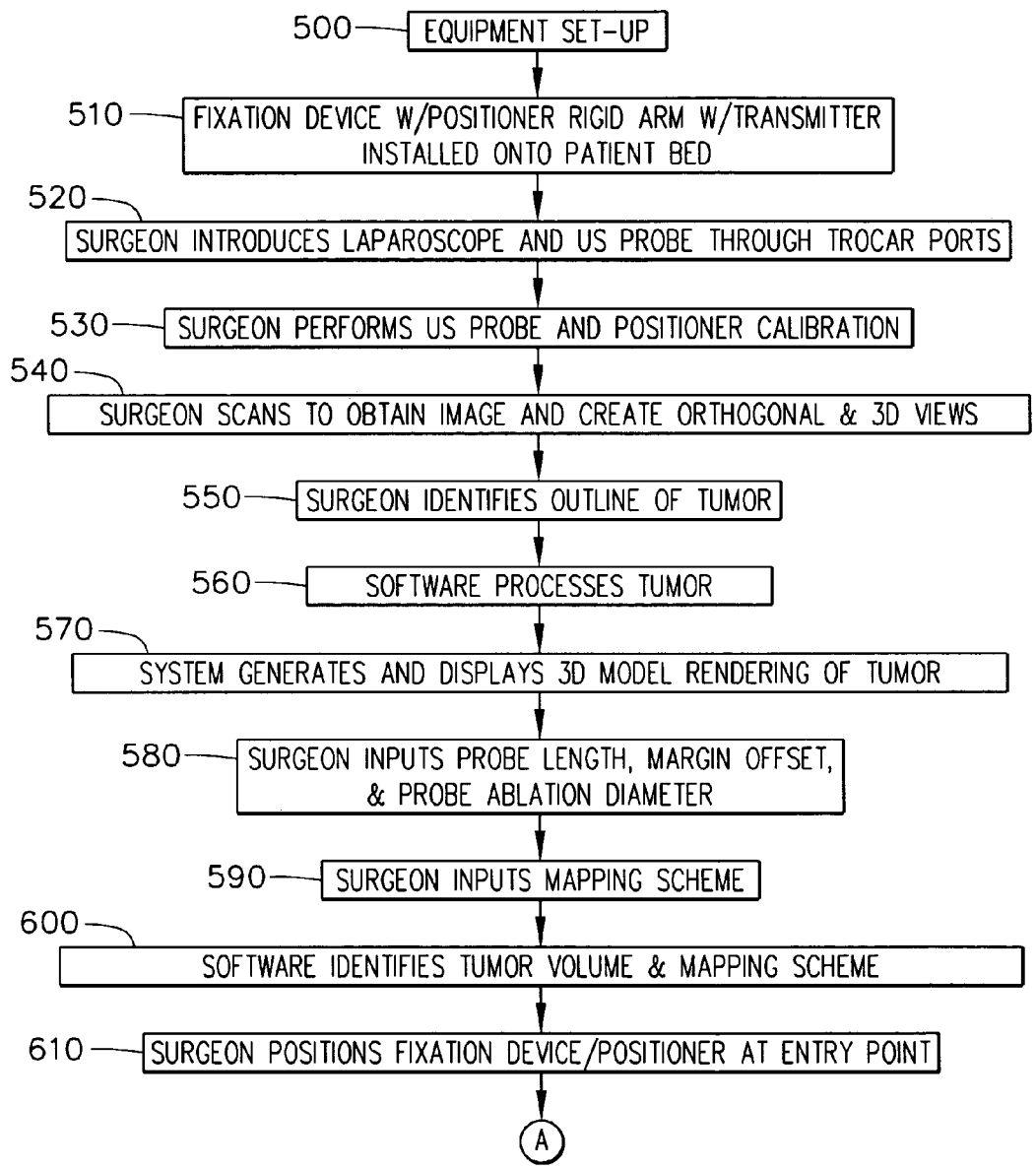
FIGS. 10A and 10B are a procedure flow diagram of a second aspect of the invention.
Figure 10B:
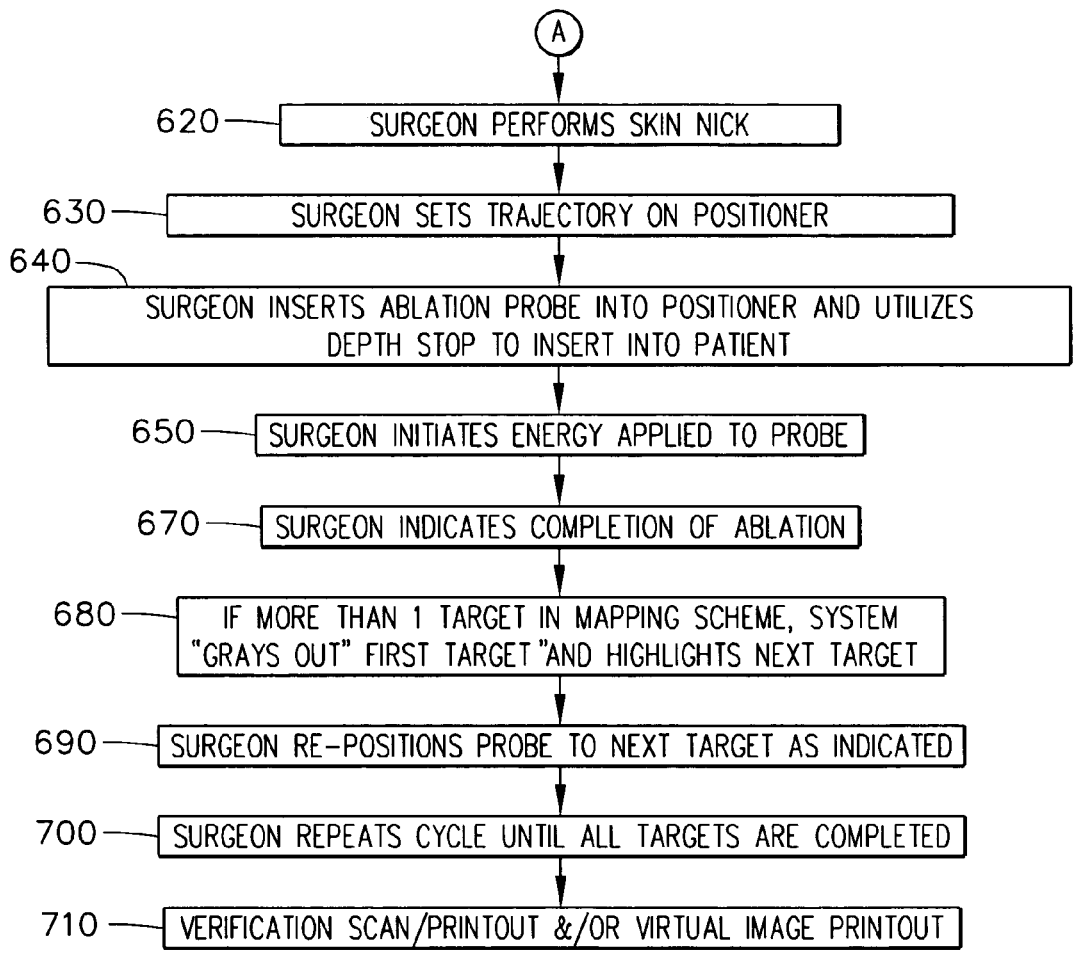

Referring now to FIGS. 10A and 10B, a second aspect of the invention relates to a method for treating tumors or lesions in a patient. One embodiment of the method begins with setting up the equipment at step 500. The procedure set-up for a laparoscopic procedure is well established and documented in independent surgical references. Any manufacturers' ablation probe may be used in this embodiment. The ablation probe 180 is utilized as presented in the manufacturer's product literature. The method is not limited to the use of ablation probes and may apply to the guidance of any surgical device. In one embodiment, as illustrated in FIGS. 1B and 2, the mobile cart 210 containing the keyboard 161, mouse 162, and display screen 160 is present and connected to the control device 140. The ultrasound probe bracket 125 with the ultrasound probe sensor 120 is mounted on the ultrasound probe 110. The ultrasound system 100 and positioner sensor 155 are also connected to the control device 140. The laparoscopic camera 115 is connected to an independently operating room monitor 116.

In step 510 a fixation device 190 is mounted to the operating room table bed rail 195, such that the free, distal end of the fixation device is located proximate to the insertion point in a light friction state. The fixation device 190 has a second rigid arm 191 that supports a transmitter 192. The transmitter 192 serves as a reference point during the method and is connected to the control device 140. The positioner 150 is attached to the free end of the fixation device 190. In step 520 of the method, the surgeon passes the laparoscopic camera 115 and ultrasound probe 110 through their respective trocars to the tissue site.

In step 530 the surgeon calibrates the ultrasound probe 110 and the positioner 150. In one embodiment, the location of the ultrasound probe sensor 120 on the ultrasound probe 110 is known by the control device 140. In an alternative embodiment, the surgeon may enter information regarding the physical location of the ultrasound probe sensor 120 using the keyboard 161 and mouse 162. In one embodiment, the control device 140 the location of the positioner sensor 155 on the positioner 150 is known. In an alternative embodiment, the surgeon may enter information regarding the physical location of the positioner sensor 155. In a further alternative embodiment, the locations of the entry point 371 and exit point 372, and therefore the location and orientation of the channel 800, relative to the positioner sensor 155 may be calculated by the control device 140. To calculate the locations of the entry point 371 and exit point 372, the surgeon must first place the entry point 371 at a fixed location, such as the calibration point 193 (shown in FIG. 2). The surgeon must then pivot the positioner 150 about the entry point 371, holding the entry point 371 at the calibration point 193. During the pivot motion, the positioner sensor 155 transcribes a portion of a sphere centered at the entry point 371. By calculating the center of the sphere transcribed by the positioner sensor 155, the control device 140 is able to determine the relationship between the positioner sensor 155 and the entry point 371. Similarly, if the surgeon places the exit point 372 at the calibration point 193 and pivots the positioner 150 about the exit point 372, the control device 140 is able to determine the location of the exit point 372 relative to the positioner sensor 155. Based upon the locations of the entry point 371 and exit point 372, the control device 140 is able to calculate the trajectory of a surgical device inserted in the channel 800 of the positioner 150.

The surgeon may also calibrate the ultrasound imaging system at step 530. The control device 140 may utilize the output data generated by existing ultrasound imaging systems. The control device 140 may use the output data transmitted by the ultrasound imaging system to the display screen 160. This data may include not only the ultrasound 2D representation of a portion of the body volume, but also additional information such as the patient name. To calibrate the ultrasound system, the surgeon or technician may identify the portion of the display screen 160 containing the 2D representation of the body volume. Once this portion of the display screen is identified, the control device 140 is able to determine the relationship between the 2D representation of the body volume and the position of the ultrasound probe sensor 120 to determine the position of that 2D representation of the body volume relative to the transmitter 192 which serves as the reference point.

Figure 11:
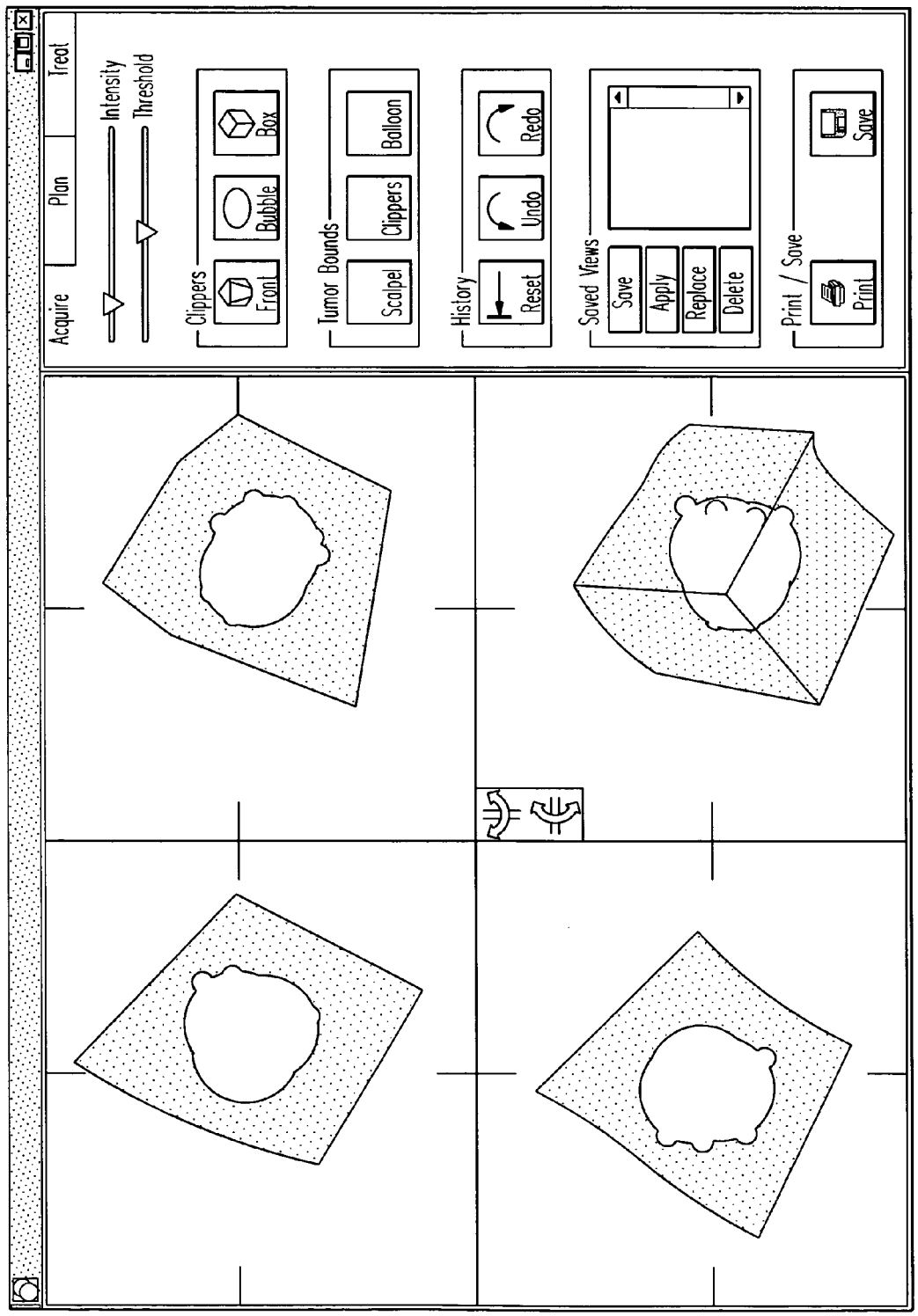
FIG. 11 is an illustration of the acquisition display screen in accordance with the second aspect of the invention.

Referring now to FIGS. 10A, 10B and 11, in step 540, the control device 140 initiates in ultrasound acquisition mode and the ultrasound probe 110 is used to capture the desired tissue image. The surgeon may use an ultrasound probe 110 to generate a 2D representation of a portion of the body volume. By moving the ultrasound probe 110, the surgeon may generate a data set consisting of a series of 2D representations of the body volume. Using location information received from the ultrasound probe sensor 120 while the ultrasound probe 110 generates the 2D representations, the control device 140 "stacks" the 2D representations to create a 3D image or model of a portion of the body volume. In acquisition mode, the surgeon is able to view the 3D image on the display screen 160 to ensure that the tumor tissue is clearly visible in the 3D image. The control device 140 may create three orthogonal views and an oblique simulated 3D view of the image on the display screen 160, as illustrated in FIG. 11. In one embodiment, the surgeon is able to generate several data sets of images and select the best data set from which to generate a treatment plan.

Figure 12:
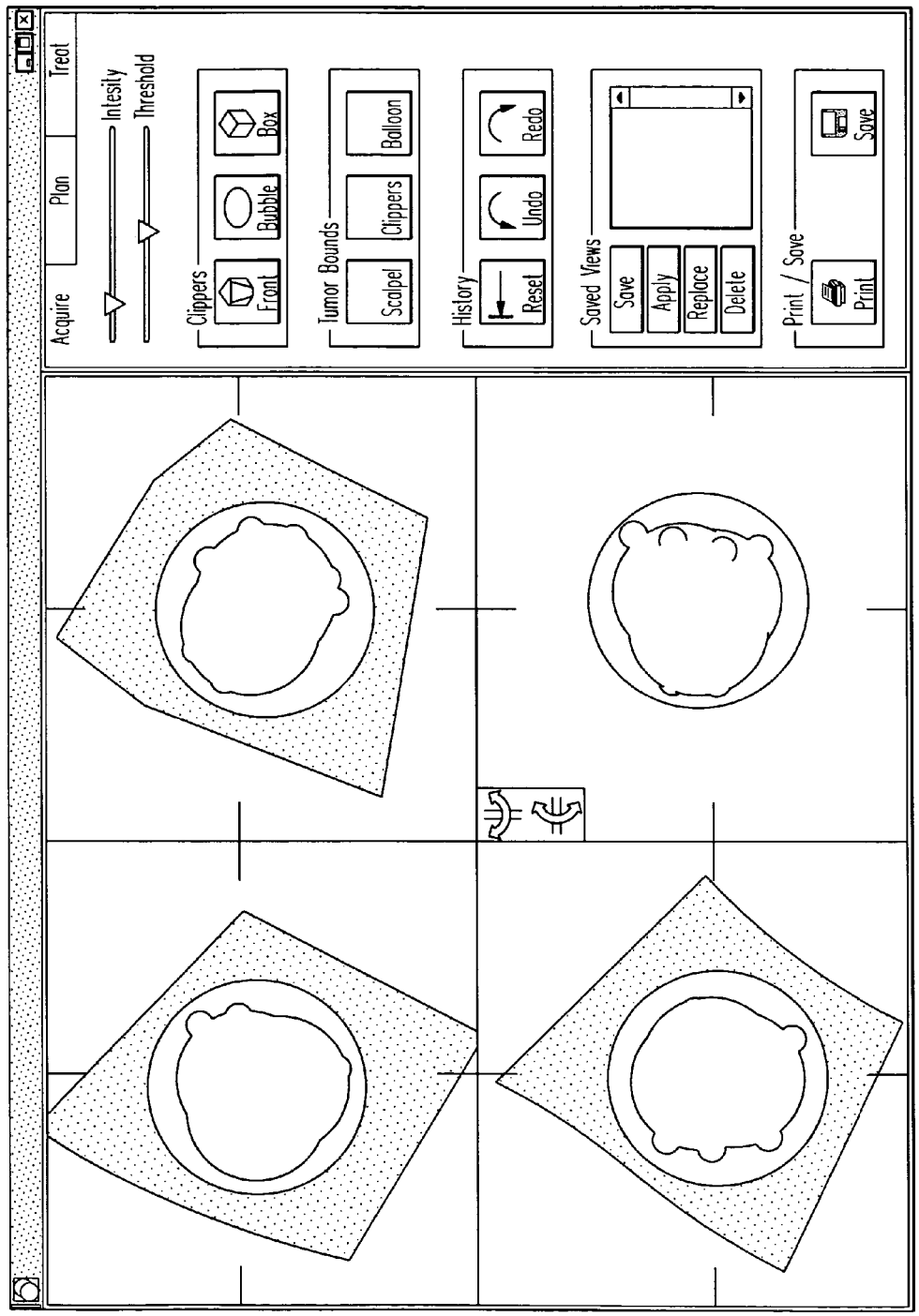
FIG. 12 is an illustration of a display screen indicating the surgeon selected tumor outline in accordance with the second aspect of the invention.

Referring now to Figures 10A, 10B and 12, in step 550 the surgeon scrolls through the 3D image manipulating the views to identify the outline of the tumor using the control device 140. In one embodiment, the surgeon is able to identify the outline of the tumor using a variety of methods, including freehand drawing using a mouse, a stylus or a light pen. Additionally, the surgeon may be able to select a circle of interest in any of the orthogonal views. By selecting circular areas in each of the orthogonal views, the surgeon may effectively outline the tissue volume. Software methods for drawing circles are well established in the prior art. In the present embodiment, the surgeon may define a circle by using a mouse to select two points on an orthogonal view. The first point defines the center of the circle. The second point, located at a distance from the first point, establishes the radius. In one embodiment, each of the three circles selected in step 550 defines a cylinder or column of data within the 3D image. The control device 140 analyzes the intersection of the three cylinders to define the tumor volume. The surgeon may also utilize additional drawing tools such as a cutting plane to define the outline of the tumor volume. By selecting two points on any one of the orthogonal views to form a line, the surgeon may define a cutting plane. By selecting a third point on one side of the plane, the surgeon may cut away or eliminate all of the data on that side of the cutting plane. Alternative embodiments may include utilizing additional geometric shapes and methods for defining such shapes. One skilled in the art will appreciate that there are numerous methods for defining volumes.

Once the outline of the tumor has been established, the control device 140 uses the outline to process the tumor volume in step 560. The control device 140 may remove all data outside of the tumor outline from the display screen 160, as illustrated in the simulated 3D view shown in FIG. 12. The control device 140 may also analyze the data within the tumor outline identified by the surgeon. Generally, the density of tumor tissues varies from that of normal tissue. By comparing relative tissue density, as represented by pixel intensity, the control device 140 is able to identify tumor tissue and further refine the tumor outline.

In an alternative embodiment, the surgeon may identify a point on the display screen 160 as being part of the tumor. The control device 140 may compare the tissue density of the point selected by the surgeon to the density of the surrounding tissue. By determining the areas in the image where the tissue density changes, the control device 140 may identify the tumor volume. The control device 140 may then highlight the perimeter of the tumor volume in each of the views presented on the display screen 160. In step 570, the tumor volume is presented on display screen 160 as a 3D rendered view which can be manipulated and measured.

The surgeon may apply a margin offset to expand the tumor volume for ablation planning in step 580. Based on this expanded volume, the surgeon may select an appropriate ablation probe 180 and inputs the selected probe's ablation parameters, such as length, ablation diameter and ablation diameter offset from the physical probe tip. The parameters may be entered into the control device 140 using the keyboard 161 and the mouse 162.

Figure 13:
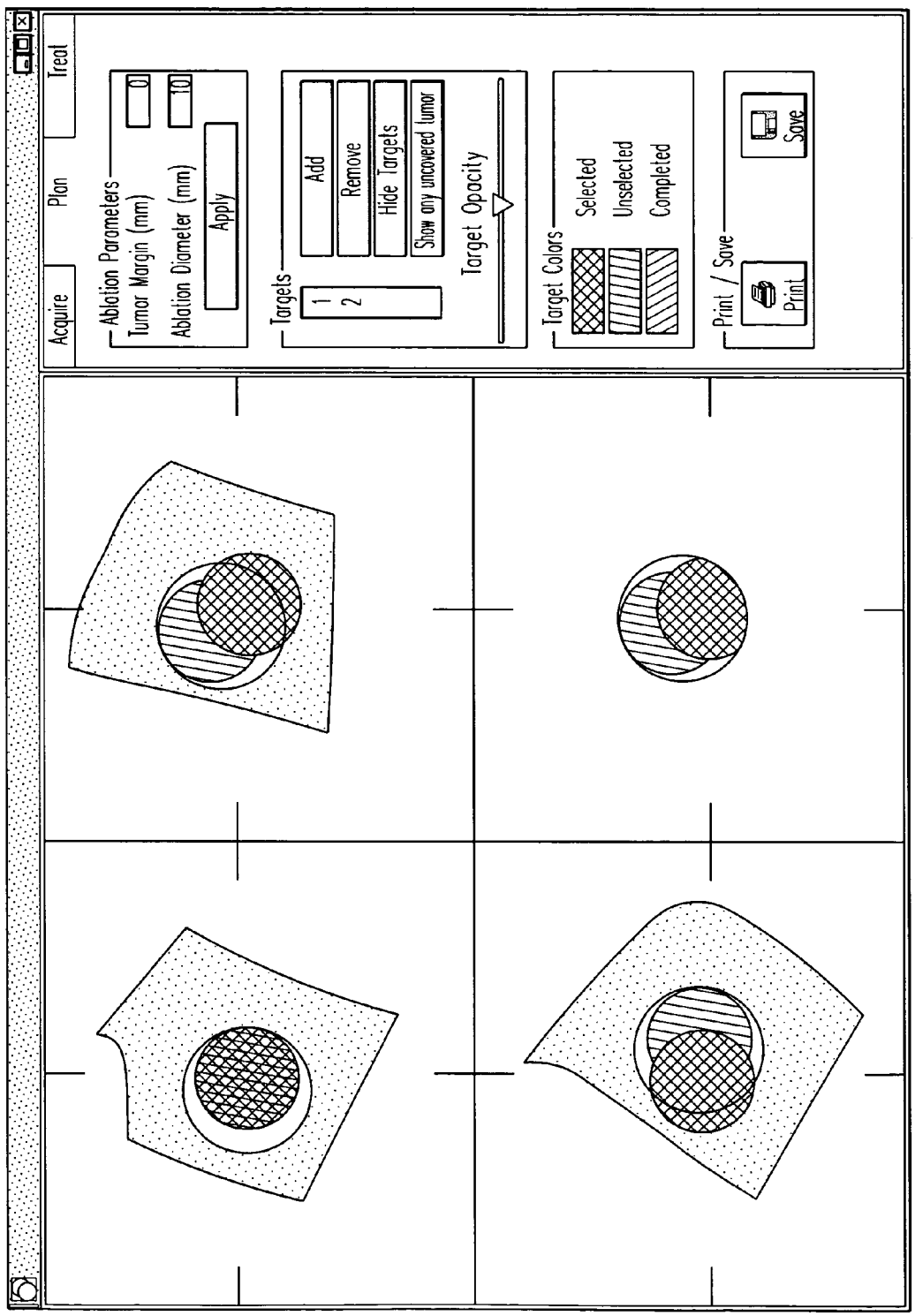
FIG. 13 is an illustration of a display screen indicating target treatment volumes in accordance with the second aspect of the invention.

Referring now to FIGS. 10A, 10B and 13, in step 590 of the method, once the surgeon is satisfied with the images acquired in the acquisition mode, the control device 140 is updated to the planning mode. As used herein, a treatment volume is the volume of tissue that is affected by the ablation probe 180 when the ablation probe 180 is held stationary and energized. A target treatment volume is a volume of tissue that is to be ablated or treated with the ablation probe. In planning mode, the surgeon may place target treatment volumes onto the tumor volume based on the ablation parameters of the ablation probe 180 until the desired coverage or "mapping scheme" is achieved. The surgeon may select the position of target treatment volumes using an input device such as a mouse 162 to direct a cursor on the display screen 160. A numbered reference table on the display screen 160 lists the target treatment volumes in the order in which they are to be treated. By manipulating the reference table, the surgeon may alter the treatment order or delete target treatment volumes. Software in the control device 140 enables assessment of the tumor volume coverage. In one embodiment, the control device 140 indicates any portions of the tumor volume not incorporated in any of the target treatment volumes. In an alternative embodiment, the control device 140 may automatically calculate the target treatment volumes and generate a mapping scheme. In step 600, the control device 140 dynamically displays the individual target treatment volume locations on the orthogonal and 3D views. The treatment volumes may be color-coded to allow the surgeon to distinguish between the selected treatment volume, target treatment volumes that have already been treated and target treatment volumes that are yet to be treated.

Figure 14:
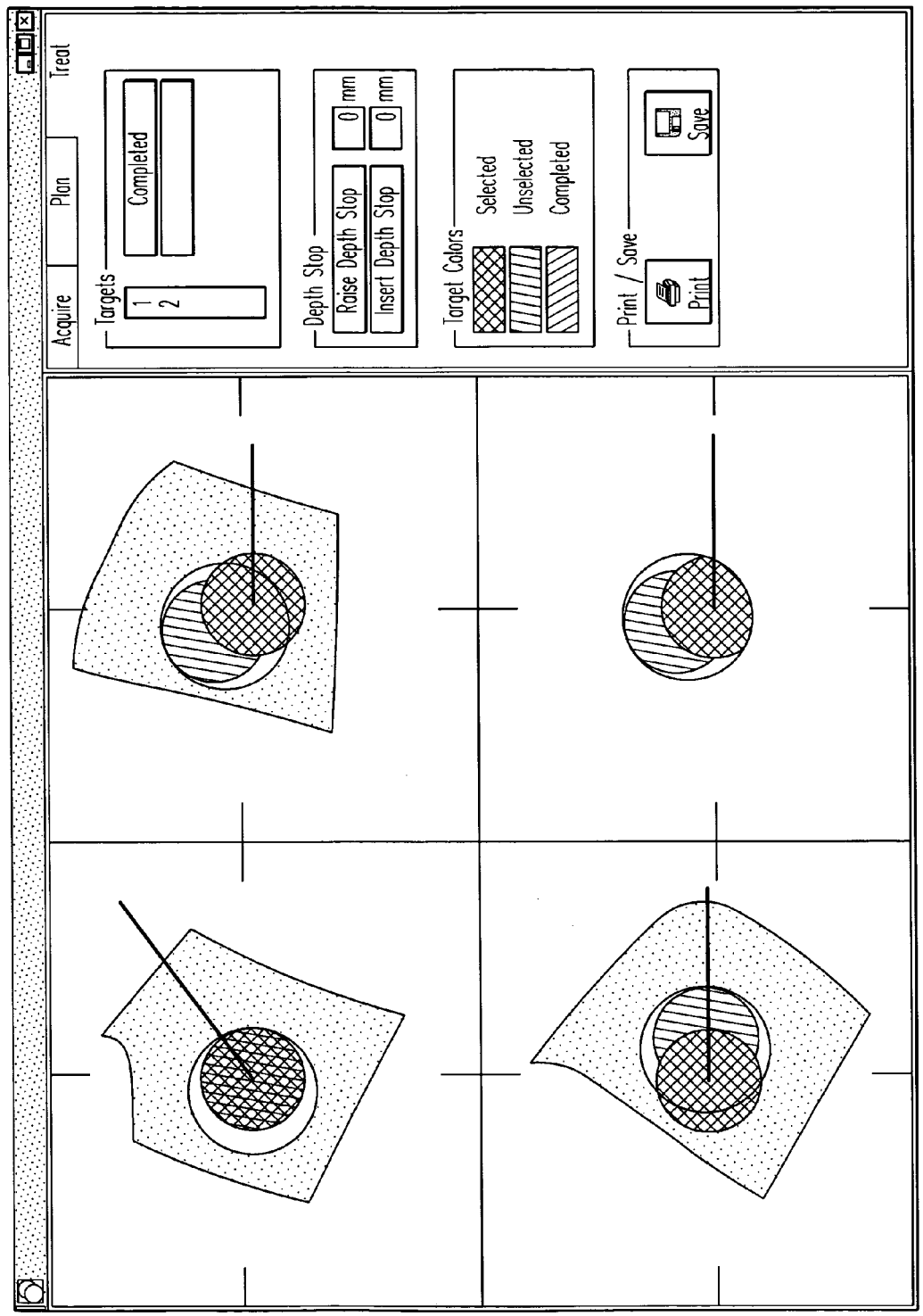
FIG. 14 is an illustration of a display screen indicating surgical device guide trajectory in accordance with the second aspect of the invention.

Referring now to FIGS. 10A, 10B and 14, in step 610, after the mapping scheme is defined, the control device 140 is updated to treatment mode. In treatment mode, the selected treatment volume, which is the next target treatment volume to be treated, is highlighted and the positioner trajectory is indicated on the display screen 160. The trajectory is an imaginary straight ray emanating from the positioner 150 indicating the projected path of the ablation probe 180 in the patient. The trajectory line is updated on the display screen as the positioner 150 is moved. The control device 140 is able to calculate the positioner trajectory 150 based upon the position and orientation of the positioner sensor 155 relative to the transmitter 192, which serves as the reference point. The positioner sensor 155 is in a fixed relation to the channel 800 into which the ablation probe 180 will be inserted. As discussed above, the 3D image of the body volume was generated by the control device 140 using the transmitter 192 as a reference point. This common reference point allows the control device 140 to project the trajectory of the positioner 150 onto the orthogonal and simulated and 3D views on the display screen 160.

Using the projected trajectory, the surgeon may select the insertion point for the ablation probe 180. The positioner 150 may be moved over the skin surface and angle of the outer stem 310 may be adjusted until the positioner trajectory and insertion point are in the desired location. Once the positioner 150 is at the desired insertion point, the peelable cover 355 is removed from the flexible stabilizer 350 and the positioner 150 is pressed lightly against the patient 170. The patient adhesive 317 on the flexible stabilizer will cause the positioner 150 to adhere to the patient 170. The fixation device 190 may also be locked into position. In alternative embodiments, the positioner 150 may be held in place solely by a fixation device 190, or by the flexible stabilizer 350.

Referring now to FIGS. 8A and 8B, in a further alternative embodiment the transmitter 178" may be contained within a clamp arm 260". In this embodiment, the clamp arm 260" must be held stationary during selection of the insertion point to provide a constant reference point. Once the positioner 150" is located at the insertion point the clamp arm 260" may be attached to the frame 240" of the positioner 150" where it will remain in a fixed location. At this point a new 3D image must be generated using the new reference point.

Referring now to FIGS. 5 and 10, in step 620 the frame 340 is unlatched as the snap lever 391 is disengaged from snap catch 392. The frame 340 is rotated to expose slots 410 within the holder 325. The slots 410 enable a surgeon to create a transdermal incision to permit easy insertion of the ablation probe 180. After the incision is made, the frame 340 is rotated back into place and the snap lever 391 re-engages the snap catch 392 to secure the frame 340. Alternatively, a lance may be inserted through the channel 800 to create a transdermal incision.

Referring now to FIGS. 3A, 3B and 10, in step 630, the positioner 150 trajectory is aligned with the selected treatment volume by rotating the outer stem 310 and utilizing the trajectory indicator shown on the display screen 160. In one embodiment the display screen 160 will indicate when the trajectory of the positioner 180 is aligned with the selected treatment volume. Once the tractory is aligned, the positioner 150 may be locked into position by turning the knob 380. Turning the knob 380 exposes the second depth stop button catch 390, as shown in FIGS. 6A and 6B. The display screen 160 indicates the distance from the placement of the positioner 150 on the skin to the target point for the selected treatment volume. Target point, as used herein, is the point where the tip of the ablation probe must be located to ablate a target treatment volume. In an alternative embodiment, the display screen 160 may indicate the target points for each of the target treatment volumes. The display screen 160 may also indicate when the positioner trajectory is aligned with the target point of the selected treatment volume.

Figure 7A:
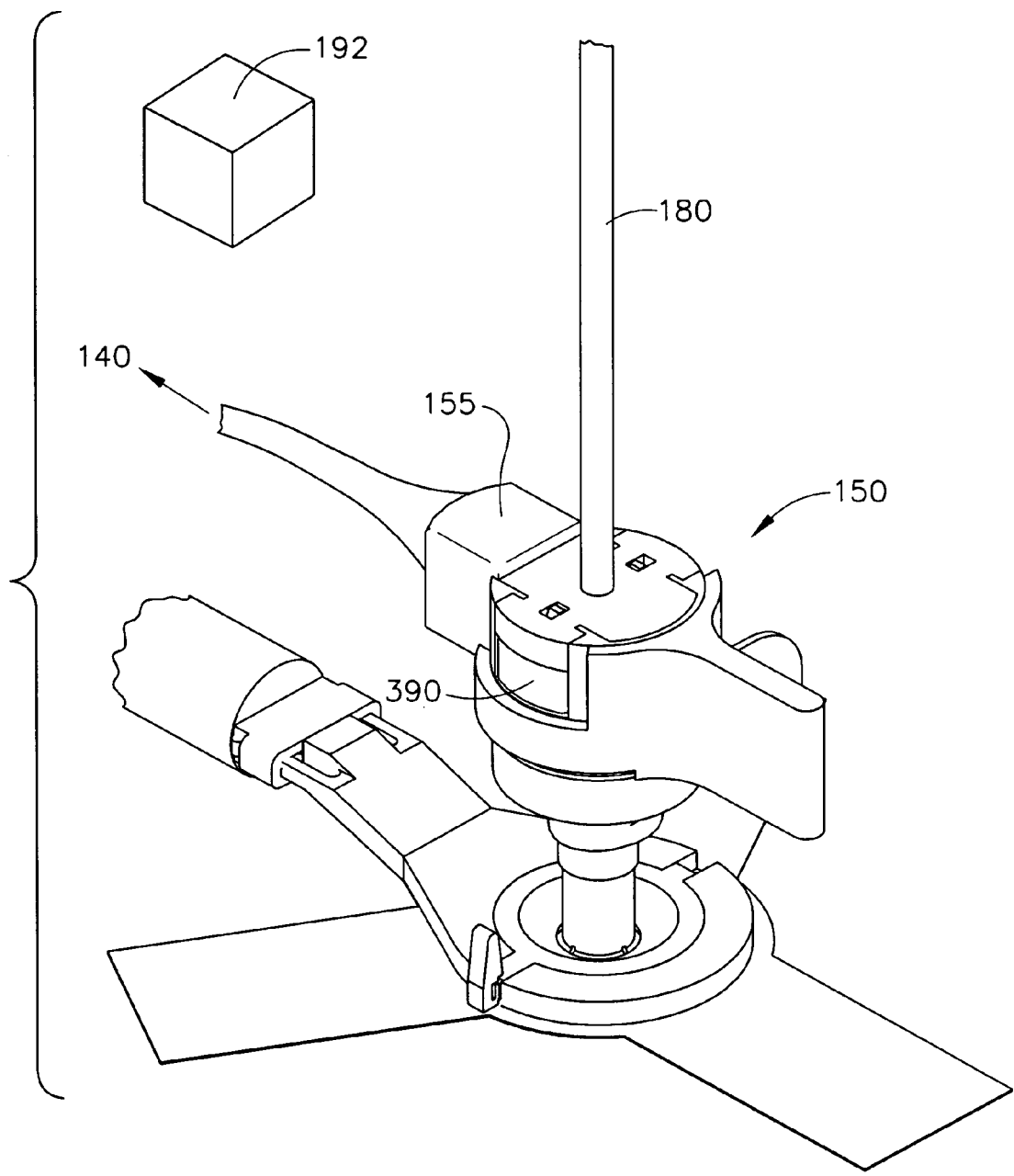
FIG. 7A is a perspective view of a first aspect of the invention depicting an inserted ablation probe.
Figure 7B:
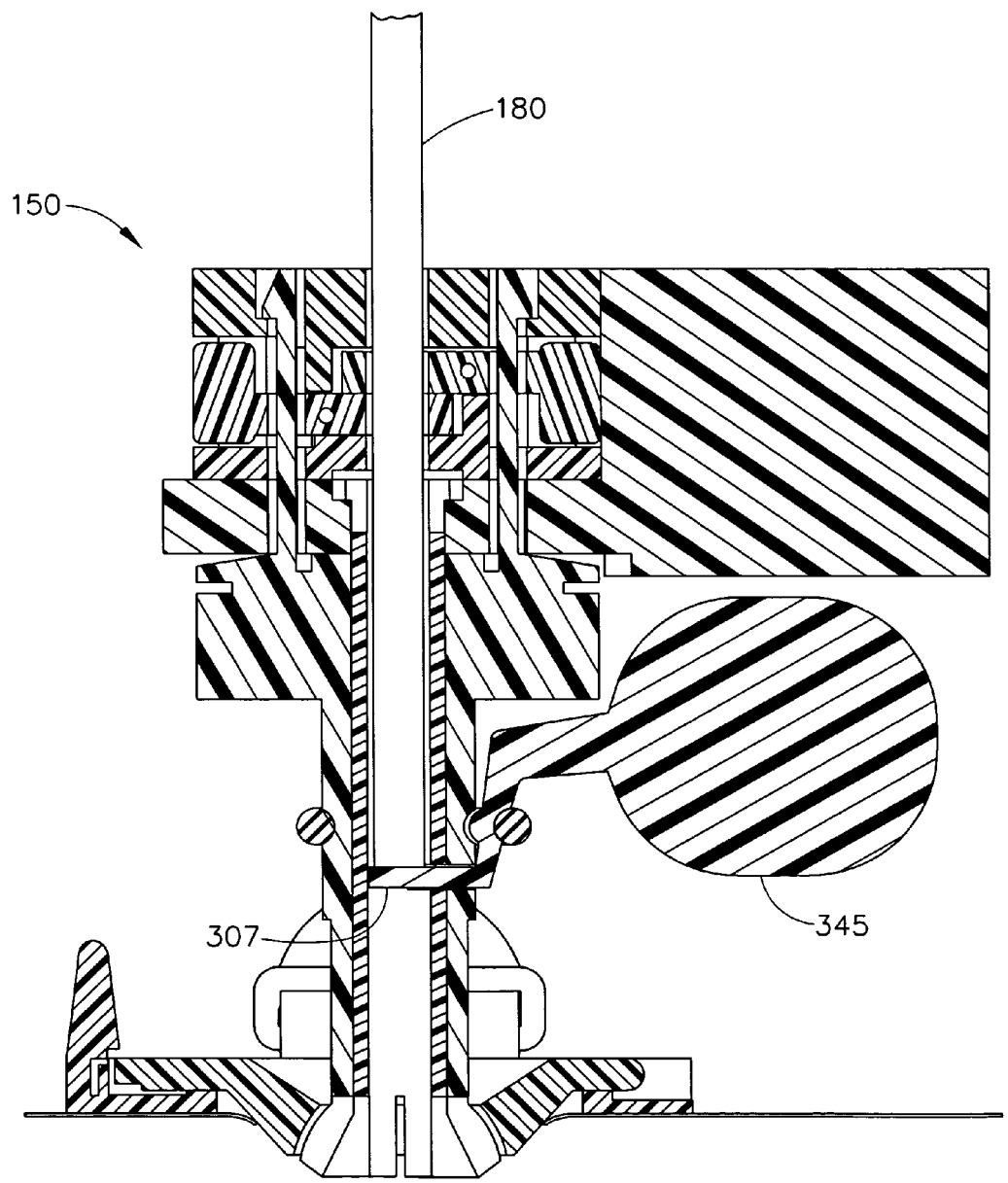
FIG. 7B is a cross section of a first aspect of the invention depicting an inserted ablation probe at the reference position.

In step 640 depth stop buttons 390 are squeezed, aligning the through holes 397 and allowing the insertion of the ablation probe 180 into channel 800. The ablation probe 180 is inserted in the positioner 150 until the distal tip of the ablation probe 180 contacts the shutter stop 307, as shown in FIGS. 7A and 7B. The positioner sensor 155 is in a fixed relation to the channel 800 in which the ablation probe 180 is seated, such that the control device 140 is able to calculate the position and orientation of the inserted ablation probe 180 based upon the position and orientation of the positioner sensor 155.

Figure 7C:
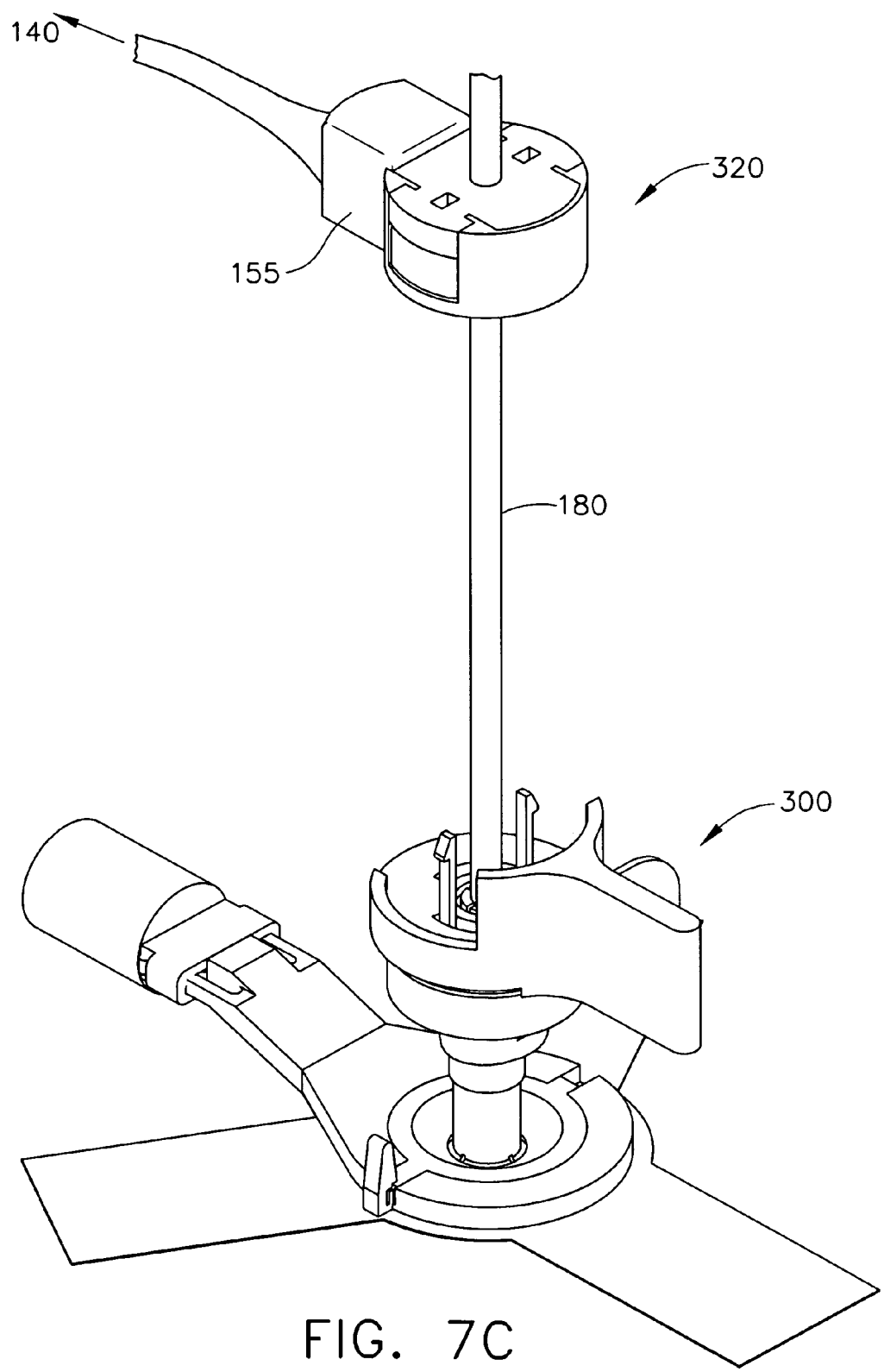
FIG. 7C is a perspective view of a first aspect of the invention depicting the depth stop in the raised position.
Figure 7D:
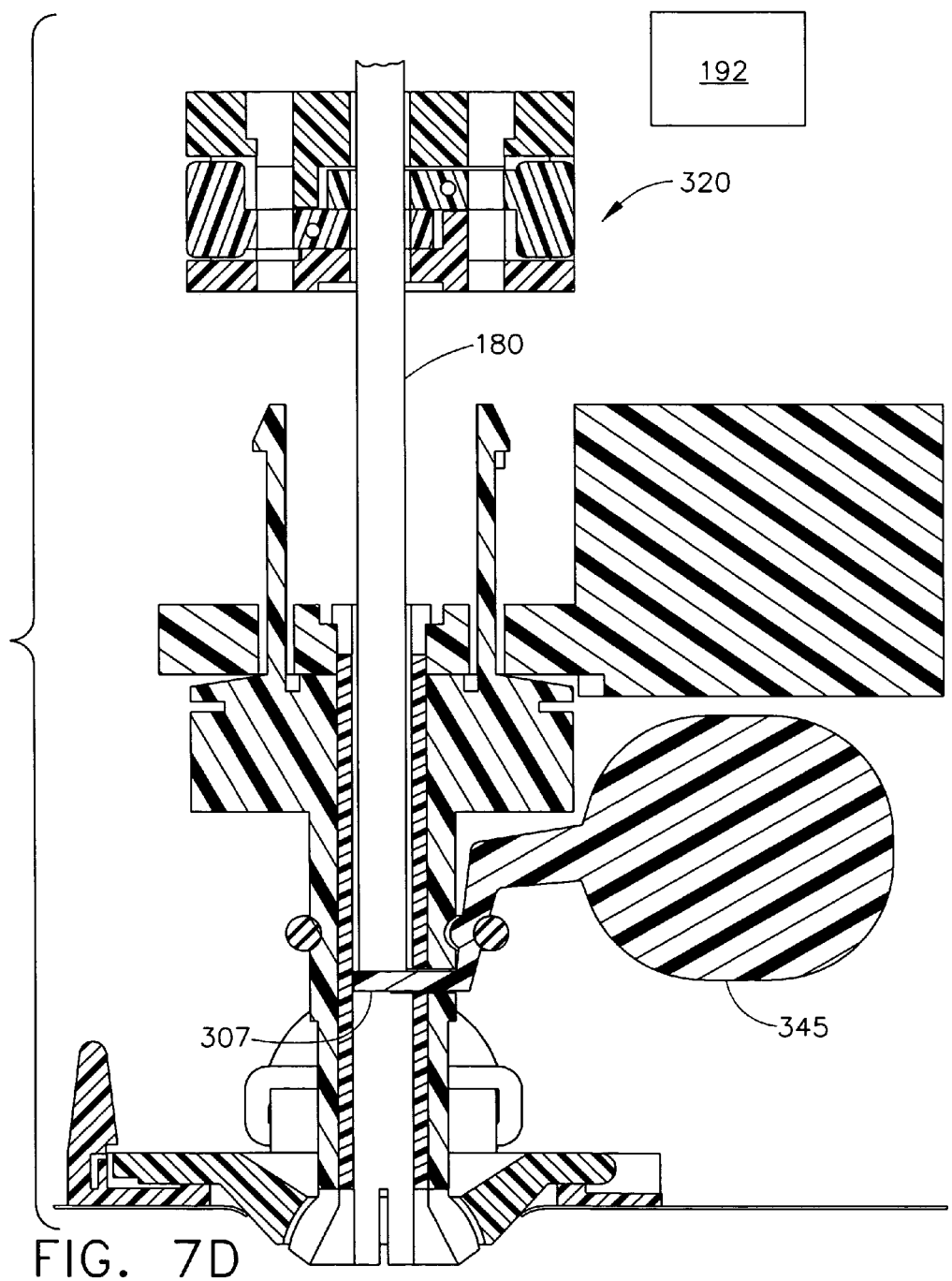
FIG. 7D is a cross section of a first aspect of the invention depicting the depth stop in the raised position.

Using the depth stop mode of the control device 140, the surgeon may position the depth stop on the ablation probe 180 such that the depth stop limits the insertion of the ablation probe 180 in to the patient to the distance from the insertion point to the target point. First, the surgeon may select raise depth stop mode using the keyboard 161 or mouse 162. In raise depth stop mode, the display screen 160 provides a readout based upon depth stop position. The readout decreases to zero as the depth stop 320 is raised along the ablation probe shaft until the height of the depth stop on the ablation probe shaft equals the depth the ablation probe must be inserted to treat the selected treatment volume. This dimension incorporates an adjustment for any offset of the effective ablation volume from the physical end of the ablation probe, as entered by the surgeon at step 580. FIG. 7C depicts a depth stop 320 raised along the ablation probe shaft. Once the depth stop 320 is raised to the appropriate height, releasing the depth stop buttons 390 will cause the through holes 397 to become misaligned. The walls of the through holes 397 will then grip the ablation probe 180 like a clamp, holding the depth stop 320 in place. FIG. 7D depicts the ablation probe 180 inserted in the positioner, in contact with the shutter stop 307 and the depth stop 320 raised to a predetermined height. The positioner sensor 155 communicates its new coordinates to the control device 140 based on its location relative to the transmitter 192.

Next, the surgeon may then select insert depth stop mode, such that the display screen 160 indicates the depth to which the ablation probe must be inserted to treat the selected treatment volume. The surgeon inserts the ablation probe 180 into the patient 170 until the depth stop 320 returns to its reengaged location on the positioner 150 and the display screen 160 depth readout is equal to zero. At step 650, once the ablation probe 180 is located at the proper position to treat the selected treatment volume, the surgeon energizes the ablation probe 180 to treat the target volume. After the ablation cycle is completed in step 670, the surgeon may select the selected treatment volume using the mouse 162 to indicate the treatment of the selected treatment volume is complete.

In step 680, if there are any un-ablated target treatment volumes, the control device 140 advances to the next numbered target treatment volume. The display screen 160 highlights the next selected treatment volume and grays the completed target treatment volume in the onscreen images and in the reference table listing of target treatment volumes.

In step 690 of the process, the surgeon depresses the depth stop buttons 390 and removes the ablation probe 180 from the tissue. Turning the knob 380 unlocks the positioner trajectory. In step 700, the process returns to step 630 and repeats the trajectory and treatment until all the target treatment volumes are ablated. The surgeon has the option to re-scan the tumor tissue at any point. In one embodiment the control device 140 will indicate unablated tumor tissue on the display screen 160.

In step 710, the control device 140 allows the surgeon to store of any of the ultrasound images, orthogonal 2D or 3D views, or ablation plans. The information may be stored in a hard drive, a disk drive, a CD or any other storage medium known in the art. A screen capture may be taken at any point during the method and printed at a later time. As used herein, a screen capture transfers the current image from the display screen 160 and saves it to a graphics file for later use.

Method for Treating a Tumor Using the Tumor as the Fiducial

A third aspect of the present invention relates to a method for ablating tumors within a patient using the tumor as a fiducial. As used herein, a fiducial is a reference point. By holding ultrasound probe in a fixed position during a complete respiratory cycle, the imaging system is able to capture the motion of the tumor motion due to respiration. The system may create an image of the tumor at its longest dwell time. As used herein, dwell time is the brief pause between inhalation and exhalation at each end of the respiratory cycle. The dwell time image is used to generate the ablation plan. The ultrasound probe is used to monitor the respiration cycle of the patient as the control device 140 synchronizes the motion of the tumor with the ablation plan image. The control device 140 indicates to the surgeon when the moving tumor is aligned with the ablation plan image. In one embodiment the control device 140 will alert the surgeon slightly before the tumor is aligned with the ablation plan image to allow for the reaction time of the surgeon. By inserting the surgical device only when the tumor is aligned with the ablation plan image, this method removes error due to respiration motion.

Figure 15A:
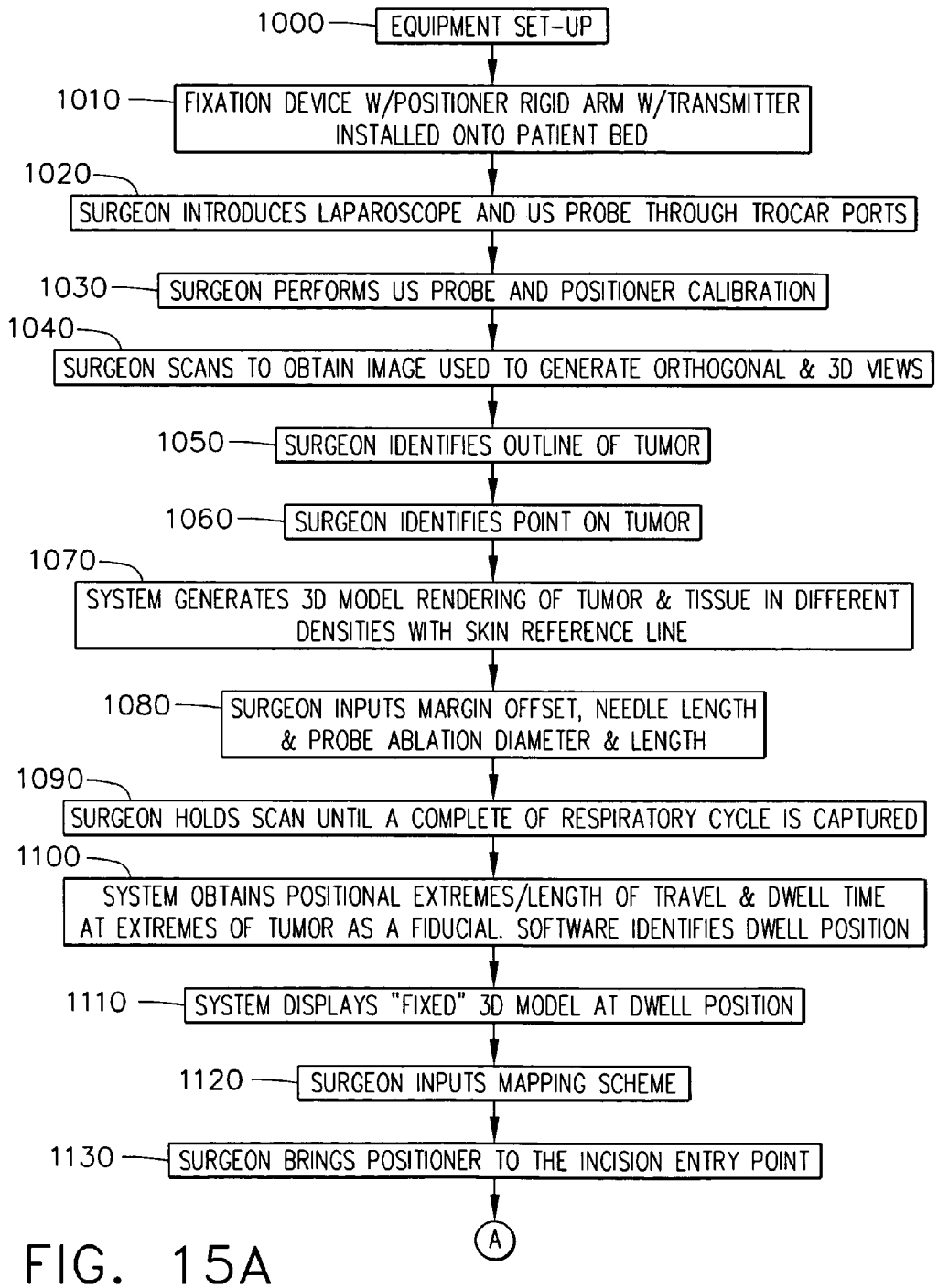
FIGS. 15A and 15B are a procedure flow diagram of a third aspect of the invention.
Figure 15B:
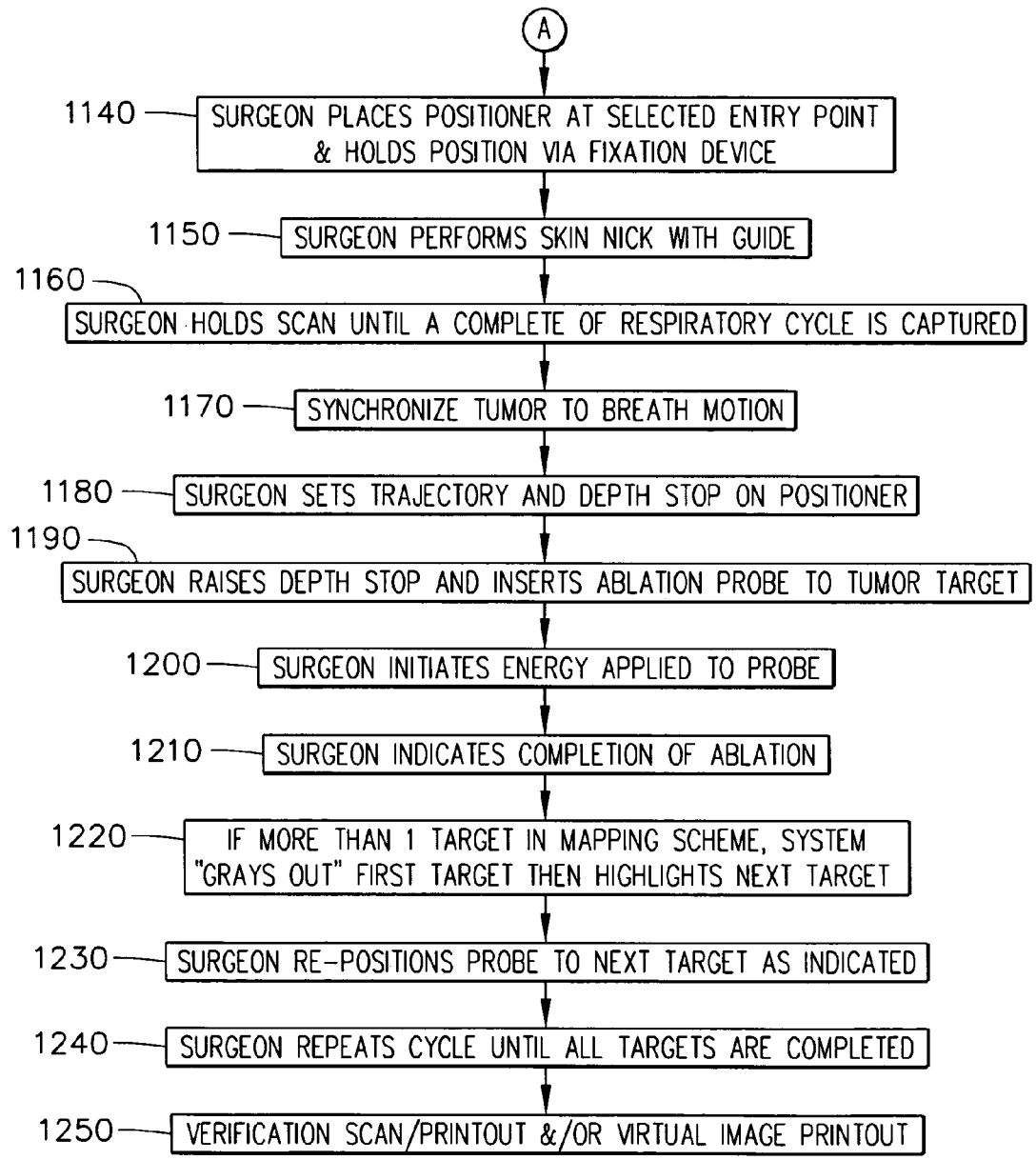

Referring now to FIGS. 15A and 15B, one embodiment of the third aspect of the invention begins at step 1000 with setting up the equipment. The procedure set-up for a laparoscopic procedure is well established and documented in independent surgical references. As shown in FIG. 1B, the mobile cart 210 containing the keyboard 161, mouse 162, and display screen 160 is present and connected to the control device 140. Ultrasound probe bracket 125 with ultrasound probe sensor 120 is mounted on the ultrasound probe 110. The ultrasound system 100 and the positioner sensor 155 are connected to the control device 140. The laparoscopic camera 115 is connected to an independently operating room monitor 116.

In step 1010 a fixation device 190 is mounted to the operating room table bed rail 195 such that the free, distal end is located proximate to the insertion point. The fixation device 190 is in a light friction state to allow for further adjustments in position. The fixation device 190 has a second rigid arm 191 that supports the transmitter 192. The transmitter 192 acts as a reference point and is connected to the control device 140. The positioner 150 is attached to the free end of the fixation device 190. In step 1020 of the method, the surgeon passes the laparoscopic camera 115 and ultrasound probe 110 through their respective trocars to the tissue site.

Referring now to FIGS. 11, 15A and 15B, in step 1030 the surgeon calibrates the ultrasound probe 110 and positioner 150, as described in detail above. In step 1040, the control device 140 initiates to the ultrasound acquisition mode and the ultrasound probe 110 is used to capture the desired tissue image. As the ultrasound probe 110 moves it generates a data set consisting of a series of 2D representations of the body volume. These 2D representations are stacked to create a 3D image of a portion of the body volume, as described in detail above with respect to the second aspect of the present invention. The control device 140 creates three orthogonal 2D views and an oblique simulated 3D view on the display screen 160. In acquisition mode the surgeon is able to view the simulated 3D view and the 2D views on the display screen 160 and ensure that the tumor tissue is completely covered by the image of the body volume. In one embodiment, the surgeon is able to generate several images and select the best image from which to create a treatment plan.

Referring now to FIGS. 12, 15A and 15B, in step 1050 the surgeon scrolls through the 3D image manipulating the views to identify the outline of the tumor using the control device 140. In one embodiment, the surgeon is able to identify the outline of the tumor using a variety of methods, including freehand drawing using a mouse, a stylus or a light pen. Additionally, the surgeon may be able to select a circle of interest in any of the orthogonal views. By selecting circular areas in each orthogonal view, the surgeon is effectively able to outline the tissue volume. Software methods for drawing circles are well established in the prior art. In one embodiment, the surgeon may define a circle by selecting two points on an orthogonal view. The first point defines the center of the circle. The second point, located at a distance from the first point, establishes the radius. In the present embodiment, each of the three circles selected in step 1050 defines a cylinder or column of data within the 3D image. The software analyzes the intersection of those three cylinders to define the tumor volume. The surgeon may also utilize additional drawing tools such as a cutting plane to define the outline of the tumor volume. By selecting two points on any one of the orthogonal views to form a line, the surgeon may define a cutting plane. By selecting a third point on one side of the plane, the surgeon may cut away or eliminate all of the data on that side of the cutting plane. Alternative embodiments may include utilizing additional geometric shapes and methods for defining such shapes. One skilled in the art will appreciate that there are numerous methods for defining volumes. The present invention is not intended to be limited to a particular method.

Once the outline of the tumor has been established, in step 1060 the surgeon identifies a point on the tumor which serves as the fiducial or reference point. The control device 140 uses the outline to process the tumor volume in step 1070. The control device 140 may remove all data outside of the tumor outline from the display screen 160, as illustrated in the simulated 3D view shown in FIG. 12. In another alternative embodiment of the third aspect of the invention, the control device 140 may analyze the data within the outline identified by the surgeon. By comparing relative tissue density, as represented by pixel intensity, the control device 140 is able to further define the tumor volume within the outline. In an alternative embodiment, the surgeon may identify a point on the display screen 160 as being part of the tumor. Based upon the tissue density of the selected point, the control device 140 may automatically generate an outline of the tumor volume and highlight the tumor's perimeter in each of the views presented on the display screen 160. The tumor volume is presented on display screen 160 as a 3D rendered view that can be manipulated and measured.

The surgeon may apply a margin offset to expand the tumor volume for ablation planning in step 1080. Based on this expanded volume, the surgeon may select an appropriate ablation probe 180 and input the selected probe's ablation parameters, such as length, ablation diameter and ablation diameter offset from the physical probe tip. The ablation parameters may be entered into the control device 140 using a keyboard 161 and a mouse 162.

In step 1090, the surgeon holds the ultrasound probe 110 in a fixed position while collecting image data to capture a complete respiratory cycle of the patient 170. At step 1100, the control device 140 records the positional extremes, length of travel and dwell times at the ends of the respiratory cycle. The position of the tumor volume at the longest dwell time is defined as the dwell position. At step 1110 the control device 140 generates an image of the tumor in the dwell position, referred to herein as the dwell position image. The dwell position image is depicted on the display screen 160, allowing the surgeon to rotate, pass cutting planes, enlarge or otherwise manipulate the dwell position image.

Once the surgeon is satisfied with the images collected in the acquisition mode, the control device 140 is updated to the planning mode to generate a mapping scheme at step 1120.

The surgeon may place target treatment volumes onto the tumor volume based on the ablation parameters of the ablation probe 180, until the desired coverage or mapping scheme is achieved. In one embodiment, the surgeon may select the position of target treatment volumes on the display screen 160 using an input device such as a mouse 162 to direct a cursor on the display screen 160. Software in the control device 140 enables assessment of the tumor coverage. A numbered reference table lists each of the selected target treatment volumes in the order in which they are to be treated. By manipulating the reference table, the surgeon may alter the treatment order or delete target treatment volumes. In an alternative embodiment the control device 140 may automatically calculate target treatment volumes and generate a mapping scheme. The control device 140 dynamically displays the individual target treatment volume locations on the orthogonal and 3D images. Once the surgeon is satisfied with the mapping scheme, the control device 140 is updated to treatment mode and the initial selected treatment volume is highlighted.

At step 1130, the surgeon moves the positioner 150 to the area of the incision. The display screen 160 indicates the positioner 150 trajectory and the selected treatment volume. Using the projected trajectory, the surgeon may select the insertion point for the ablation probe 180. At step 1140, with the fixation device 190 still in a light friction state, the peelable cover 355 is peeled off the flexible stabilizer 350 to expose the patient adhesive 317. Positioner 150 is returned to the skin surface and outer stem 310 angled until the trajectory alignment and insertion point are in the desired location. The flexible stabilizer 350 is pressed lightly against the patient and the fixation device 190 is locked into position.

Referring now to FIGS. 5, 15A and 15B, at step 1150, the frame 340 is unlatched as snap lever 391 is disengaged from snap catch 392. The frame 340 is rotated to expose slots 410 within holder 325. The slots 410 enable the surgeon to create a transdermal incision to permit easy insertion of the ablation probe 180 through the skin. After the incision is made, the frame 340 is rotated back into place and the snap lever 391 re-engages snap catch 392. Alternatively, a lance may be inserted through the channel 800 to create the transdermal incision, eliminating the need to rotate the frame 340.

At step 1160 the surgeon once again holds the ultrasound probe 110 in a fixed position to capture a complete respiratory cycle and determine the positional extremes of the tumor during respiration of the patient. At step 1170 the surgeon directs the control device 140 to capture one or more respiratory cycles. Due to the anesthesia, the patient's breathing rate is consistent and controlled and the control device 140 is able to analyze the ultrasound images to monitor the respiratory cycle of the patient. In an alternative embodiment, respiratory cycle may be monitored using a motion detector or accelerometer attached to the chest of the patient 170. Additional methodologies for monitoring respiration are known in the prior art. After monitoring several respiratory cycles the control device 140 is able to determine when the tumor will be in the dwell position. The control device 140 controls an indicator that signals the surgeon that the tumor is approaching the dwell position. The indicator may be implemented using audio or visual cues, such as a simple light or a moving bar to signal that the respiratory cycle is in the respiratory dwell period. Because the mapping scheme was generated using the dwell position image, the respiratory dwell is now synchronized with the ablation mapping scheme. The surgeon uses the indicator to time the insertion of the ablation probe 180. In one embodiment the control device 140 will allow for a delay due to the reaction time of the surgeon when indicating that the tumor is approaching the dwell position. By inserting the ablation probe 180 when the tumor is at the dwell position, the accuracy of ablation probe placement is increased by eliminating error due to tissue movement caused by respiration.

At step 1180 the ablation probe 180 is placed into the positioner 150 and the target trajectory finalized. In one embodiment the display screen 160 will indicate when the trajectory of the positioner 180 is aligned with the selected treatment volume. Once the tractory is aligned, it is locked into position by turning the knob 380. At step 1190 the depth stop 320 is raised to a predetermined position, as described in detail above with respect to the second aspect of the present invention. The surgeon then waits for the signal from the control device 140 indicating that the tumor is in the dwell position and then inserts the ablation probe 180 until the depth stop 320 is seated within the positioner 150. Then at step 1200, the surgeon energizes the probe to ablate the selected treatment volume. At step 1210, upon completion of the ablation cycle, the surgeon may select the selected treatment volume using the mouse 162 to indicate the treatment of that target treatment volume is complete.

At step 1220, if there are additional target treatment volumes, the control device 140 advances to the next numbered target treatment volume, highlights its location and grays the completed target treatment volume in the views on the display screen and in the reference table. At step 1230 the surgeon depresses the depth stop buttons 390 and removes the ablation probe 180 from the tissue. The surgeon turns the knob 380 to unlock the positioner 150 and adjust the trajectory. At step 1240, the process is repeated by returning to step 1180 until all the target treatment volumes are ablated. The surgeon has the option to generate additional images of the tumor tissue at any time. At step 1250, the surgeon may elect to store of any of the ultrasound images, orthogonal or 3D views or the mapping scheme. A screen capture may also be taken at any time for printing at a later time.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to ablation of tumors, but it will be understood the present invention has additional applicability. Moreover, the structure of each element associated with the present invention can be alternatively described as a means for providing the function performed by the element. It will be understood that the foregoing description is provided by way of example, and that other modifications may occur to those skilled in the art without departing from the scope and spirit of the appended claims.

What is claimed:

1. A method for treating tissue in a body volume with a surgical device, the method comprising the steps of:
    collecting image data associated with the body volume using an imaging device;
    creating an image from the image data;
    displaying the image on a display screen;
    selecting at least one tissue target in the body volume for treatment;
    determining an effective treatment volume of the surgical device;
    determining a treatment modality for treating the tissue target with the surgical device, wherein the treatment modality is made up of a set of target treatment volumes;

displaying the set of target treatment volumes with the image during treatment of the at least one tissue target, and updating the display of the set of target treatment volumes to indicate target treatment volumes that have already been treated, and target treatment volumes yet to be treated.

2. The method of claim 1, farther including the steps of:
determining the position and orientation of the imaging device with respect to a reference point;
determining the relationship of the image to the reference point;
determining the position and orientation of the surgical device with respect to the reference point; and
indicating a trajectory of the surgical device with respect to the image on the display screen.

3. The method of claim 2, further including positioning the surgical device in the body volume based upon the trajectory, and treating the tissue target with the surgical device.

4. The method of claim 3, wherein positioning the surgical device includes placing the surgical device in a surgical device guide.

5. The method of claim 3, wherein the steps of sensing the position and orientation of the imaging device and the surgical device include:
affixing a first positional indicator to a predetermined point associated with the imaging device; and
affixing a second positional indicator to a predetermined point associated with the surgical device.

6. The method of claim 5, wherein the first and second positional indicators are magnetic sensors.

7. The method of claim 5, wherein the first and second positional indicators are optical sensors.

8. The method of claim 3, wherein treating the tissue target includes:
providing a surgical device guide having an adjustable stop for limiting the distance the surgical device may be inserted in the body volume;
placing a positional indicator at a first position associated with the surgical device guide;
placing the positional indicator at a second position associated with the adjustable stop;
determining the position of the positional indicator in the first and second positions; and
setting the adjustable stop so that the surgical device can be inserted a predetermined distance.

9. The method of claim 3, further including the steps of:
collecting additional image data associated with the body volume using the imaging device;
creating an updated image from the additional image date; and
displaying the updated image on the display screen.

10. The method of claim 2, further including indicating the treatment volume on the display screen.

11. The method of claim 2, wherein the step of determining the position and orientation of the imaging device further includes the steps of:
sensing the position and orientation of the imaging device with respect to a reference point;
transmitting data indicative of the position and orientation of the imaging device with respect to the reference point to a control device;
and the step of determining the position and orientation of the surgical device further includes the steps of:
sensing the position and orientation of the surgical device with respect to the reference point; and
transmitting data indicative of the position and orientation of the surgical device with respect to the reference point to the control device.

12. The method of claim 2, wherein the surgical device is a radio frequency ablation probe.

13. The method of claim 2, wherein the surgical device is a cryogen ablation probe.

14. The method of claim 2, wherein the surgical device is a microwave ablation probe.

15. The method of claim 2, wherein the surgical device is a heated element.

16. The method of claim 2, wherein the surgical device is an ultrasound ablation probe.

17. The method of claim 2, wherein the imaging device is an ultrasound transducer.

18. The method of claim 1, wherein the treatment modality is determined by a control device.

19. The method of claim 1, further including the steps of determining a volume of the tissue target and increasing the volume of the tissue target by a margin offset.

20. The method of claim 1, further including inputting information regarding the surgical device for determining the treatment volume.

21. The method of claim 1, further includes indicating an order in which each of the set of target treatment volumes are to be treated, and wherein the surgical device is sequentially positioned to treat each of the set of target treatment volumes in the indicated order.

22. The method of claim 1, further including the step of dynamically color-coding the set of target treatment volumes to indicate a next target treatment volume to be treated, the target treatment volumes that have already treated, and the target treatment volumes yet to be treated.

23. The method of claim 1, further including the step of indicating a target point for at least one of the set of target treatment volumes on the display screen, where the target point indicates a position of the surgical device to effect treatment of the at least one of the set of target treatment volumes.

24. The method of claim 23, farther including the steps of adjusting the trajectory and indicating the intersection of the trajectory and the target point of at least one of the set of target treatment volumes.

25. The method of claim 1, wherein the step of displaying the image further includes displaying an orthogonal view of the image, a simulated three dimensional view of the image or a combination thereof.

26. The method of claim 1, further including removing portions of the image outside of the tissue target from the display screen.

27. The method of claim 1, further including the step of storing the image, the treatment modality or a combination thereof in a storage medium.

28. A system for treating tissue in a body volume with a surgical device, the system comprising:
an imaging device;
a control device; and
a display screen;
wherein the control device is programmed to perform the steps of:
creating an image from image data associated with the body volume collected by the imaging device;
displaying the image on the display screen;
selecting at least one tissue target in the body volume for treatment;
determining an effective treatment volume of the surgical device;

determining a treatment modality for treating the tissue target with the surgical device,
wherein the treatment modality is made up of a set of target treatment volumes each to be treated in sequence by a discrete application of the surgical device; and
displaying the set of treatment volumes on the image during treatment, the set of target treatment volumes indicating the treatment status of each of the target treatment volumes.

29. The system of claim 28, further including a surgical device guide.

30. The system of claim 29, wherein the imaging device includes a first positional indicator and the surgical device guide includes a second positional indicator.

31. The system of claim 30, wherein the surgical device guide further includes:
an adjustable stop for limiting the distance the surgical device can be inserted into the body;
a first fixture for the second positional indicator associated with the surgical device guide; and
a second fixture for the second positional indicator operatively associated with the stop, wherein by determining the position of the second positional indicator in the first and second fixtures, the stop can be set so that the surgical instrument can be inserted a predetermined distance into the body.

32. A system for treating tissue in a body volume with a surgical device, the system comprising:
an imaging device;
a control device;
a display screen; and
a surgical device guide including an adjustable stop for limiting the distance the surgical device may be inserted in the body volume
wherein the control device is programmed to perform the steps of:
creating an image from image data associated with a body volume collected using the imaging device;
displaying the image on a display screen;
displaying a set of treatment volumes that are updated dynamically to indicate the treatment status of each of the set of target treatment volumes during a treatment session;
determining an insertion distance for the surgical device, such that the surgical device may be used to treat a selected tissue target in the body volume; and
determining a position of the adjustable stop such that the adjustable stop can be set so that the surgical device may be inserted the insertion distance.

* * * * *

UNITED STATES PATENT AND TRADEMARK OFFICE
CERTIFICATE OF CORRECTION

PATENT NO.          : 7,452,357 B2
APPLICATION NO. : 10/971419
DATED                   : November 18, 2008
INVENTOR(S)        : James W. Voegele et al.

It is certified that error appears in the above-identified patent and that said Letters Patent is hereby corrected as shown below:

Title Page items 12 & 75

Change name of inventor James W. Vlegele TO James W. Voegele

Signed and Sealed this

Twenty-fourth Day of March, 2009

JOHN DOLL
*Acting Director of the United States Patent and Trademark Office*